(12) United States Patent
Obara

(10) Patent No.: US 10,441,147 B2
(45) Date of Patent: *Oct. 15, 2019

(54) ENDOSCOPE SYSTEM AND ANALYZING APPARATUS

(71) Applicant: HOYA CORPORATION, Tokyo (JP)

(72) Inventor: Yoshimi Obara, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/765,773

(22) PCT Filed: Nov. 2, 2016

(86) PCT No.: PCT/JP2016/082641
§ 371 (c)(1),
(2) Date: Apr. 4, 2018

(87) PCT Pub. No.: WO2017/078085
PCT Pub. Date: May 11, 2017

(65) Prior Publication Data
US 2018/0279865 A1 Oct. 4, 2018

(30) Foreign Application Priority Data
Nov. 2, 2015 (JP) .................. 2015-215520

(51) Int. Cl.
*A61B 1/05* (2006.01)
*A61B 1/06* (2006.01)
(Continued)

(52) U.S. Cl.
CPC ............ *A61B 1/05* (2013.01); *A61B 1/00009* (2013.01); *A61B 1/00096* (2013.01);
(Continued)

(58) Field of Classification Search
CPC ............ A61B 1/00009; A61B 1/00096; A61B 1/00117; A61B 1/043; A61B 1/045;
(Continued)

(56) References Cited

U.S. PATENT DOCUMENTS 9,370,297 B2   6/2016  Yokouchi et al.
9,420,153 B2   8/2016  Tanaka et al.
(Continued)

FOREIGN PATENT DOCUMENTS

JP   2002-85342 A    3/2002
WO   2013/035532 A1  3/2013
(Continued)

OTHER PUBLICATIONS

International Search Report in WIPO Patent Application No. PCT/JP2016/082641, dated Jan. 17, 2017.
(Continued)

*Primary Examiner* — Francis Geroleo
(74) *Attorney, Agent, or Firm* — Greenblum & Bernstein, P.L.C.

(57) ABSTRACT

An endoscope system includes: a light source apparatus; an endoscope having an imaging unit that includes an image sensor configured to generate color image data imaging biological tissue illuminated by light emitter by the light source apparatus; and a processor that has a first parameter generation unit configured to generate a first parameter that has sensitivity to a first feature amount of the biological tissue but does not have sensitivity to light scattering by the biological tissue based on the color image data, and a first feature amount acquisition unit configured to acquire the first feature amount based on the first parameter.

19 Claims, 9 Drawing Sheets

(51) Int. Cl.
  *A61B 1/045* (2006.01)
  *A61B 1/00* (2006.01)
  *A61B 1/04* (2006.01)
  *A61B 1/07* (2006.01)
  *A61B 5/145* (2006.01)
  *A61B 5/1455* (2006.01)
  *A61B 5/1459* (2006.01)

(52) U.S. Cl.
  CPC .............. *A61B 1/043* (2013.01); *A61B 1/045* (2013.01); *A61B 1/0638* (2013.01); *A61B 1/0646* (2013.01); *A61B 1/0669* (2013.01); *A61B 1/0676* (2013.01); *A61B 1/07* (2013.01); *A61B 5/14546* (2013.01); *A61B 5/14551* (2013.01); *A61B 1/00117* (2013.01); *A61B 5/1459* (2013.01)

(58) Field of Classification Search
  CPC ....... A61B 1/05; A61B 1/0638; A61B 1/0646; A61B 1/0669; A61B 1/0676; A61B 1/07; A61B 5/14546; A61B 5/14551; A61B 5/1459
  See application file for complete search history.

(56) References Cited

U.S. PATENT DOCUMENTS

| | | | |
|---|---|---|---|
| 2013/0096392 A1* | 4/2013 | Adams | A61B 5/0075 600/301 |
| 2014/0187881 A1 | 7/2014 | Saito et al. | |
| 2015/0099932 A1* | 4/2015 | Morimoto | H05B 33/0854 600/180 |
| 2015/0145978 A1 | 5/2015 | Chiba | |
| 2016/0120449 A1* | 5/2016 | Chiba | A61B 5/14551 600/311 |
| 2018/0000334 A1* | 1/2018 | Morishita | A61B 1/00009 |
| 2018/0000335 A1* | 1/2018 | Igarashi | A61B 1/04 |
| 2018/0279853 A1* | 10/2018 | Daidoji | H04N 13/257 |

FOREIGN PATENT DOCUMENTS

| | | | | |
|---|---|---|---|---|
| WO | 2013/172156 A1 | 11/2013 | | |
| WO | 2014/192781 A1 | 12/2014 | | |
| WO | WO-2014192781 A1 * | 12/2014 | ......... | A61B 5/14551 |

OTHER PUBLICATIONS

Written Opinion of the International Searching Authority in WIPO Patent Application No. PCT/JP2016/082641, dated Jan. 17, 2017.

* cited by examiner (A1)

(A2)

(B1)

(B2)

(C1)

(C2)

(D1)

(D2)

(E1)

(E2)

(F1)

(F2)

(G1)

(G2)

ENDOSCOPE SYSTEM AND ANALYZING APPARATUS

TECHNICAL FIELD

The present invention relates to an endoscope system and an analyzing apparatus that acquire biological information such as the concentration of a biological substance in biological tissue based on a captured image of the biological tissue.

BACKGROUND ART

An endoscope apparatus is known that includes a function for determining the concentration of a biological substance (e.g., hemoglobin) in biological tissue that is the imaging subject, based on color information in an endoscopic image. An example of this type of endoscope apparatus is disclosed in Patent Document 1.

The endoscope apparatus disclosed in Patent Document 1 calculates an indicator that indicates the total hemoglobin amount and an indicator that indicates the degree of oxygen saturation, based on color information in two endoscopic images captured using illumination light in two types of wavelength regions in hemoglobin's absorption band (Q band).

PRIOR ART DOCUMENT

Patent Document

Patent Document 1: WO 2014/192781

SUMMARY OF INVENTION

Technical Problem

Colors in biological tissue in a captured image are influenced by the scattering of illumination light by the biological tissue (referred to hereinafter as simply "scattering"). However, in the endoscope apparatus disclosed in Patent Document 1, the calculation of the indicators does not give consideration to change in spectral characteristics arising from scattering. For this reason, there has been a problem that the indicator calculation results vary depending on the amount of scattering, that is to say, the calculated indicator values include error arising from scattering.

The present invention was achieved in light of the above-described circumstances, and an object of the present invention is to provide an endoscope system and an analyzing apparatus that can correct error arising from scattering and perform precise spectroscopic analysis.

Solution to Problem

One aspect of the present invention is an endoscope system, which includes the following aspects.

Aspect 1

An endoscope system including:

a light source apparatus;

an endoscope having an imaging unit that includes an image sensor configured to generate color image data by imaging biological tissue illuminated by light emitted by the light source apparatus; and a processor that has a first parameter generation unit configured to generate a first parameter that has sensitivity to a first feature amount of the biological tissue but does not have sensitivity to light scattering by the biological tissue based on the color image data, and a first feature amount acquisition unit configured to acquire the first feature amount based on the first parameter.

Aspect 2

The endoscope system according to aspect 1, wherein the first parameter generation unit is configured to generate the first parameter based on color image data X of an image that has a component in a wavelength region that has sensitivity to the first feature amount of the biological tissue and has sensitivity to light scattering by the biological tissue, and color image data Y of an image that has a component in a wavelength region that does not have sensitivity to the first feature amount of the biological tissue but has sensitivity to light scattering by the biological tissue.

Aspect 3

The endoscope system according to aspect 2, wherein the light source apparatus is configured to emit first special light that has a different wavelength region from white light, and is absorbed by the biological tissue differently according to the first feature amount, the color image data X is first special observation image data W obtained by imaging the biological tissue illuminated by the first special light, the color image data Y is first normal observation image data R that is an R component of normal observation image data in an RGB color space obtained by imaging the biological tissue illuminated by the white light, and the first parameter is a ratio W/R of the first special observation image data W and the first normal observation image data R.

Aspect 4

The endoscope system according to aspect 2, wherein the light source apparatus is configured to emit first special light that has a different wavelength region from white light, and is absorbed by the biological tissue differently according to the first feature amount, the color image data X is first special observation image data W obtained by imaging the biological tissue illuminated by the first special light, the color image data Y is data $\alpha R$ obtained by multiplying first normal observation image data R by a coefficient set in advance, the first normal observation image data R being an R component of normal observation image data in an RGB color space obtained by imaging the biological tissue illuminated by the white light, and the first parameter is a ratio $W/(\alpha R)$ of the first special observation image data W and the data $\alpha R$.

In this case, it is preferable that the coefficient is obtained in advance by preliminary experimentation performed using a sample having a known first feature amount. In other words, before usage of the endoscope system starts, it is preferable that the processor performs preliminary experimentation using the known sample to determine the coefficient $\alpha$ and store it.

Aspect 5

The endoscope system according to aspect 2, wherein the light source apparatus is configured to emit first special light that has a different wavelength region from white light, and is absorbed by the biological tissue differently according to the first feature amount, the color image data X is first special observation image data W obtained by imaging the biological tissue illuminated by the first special light, the color image data Y is a sum R+G of first normal observation image data R and second normal observation image data G that are respectively an R component and a G component of normal observation image data in an RGB color space obtained by imaging the biological tissue illuminated by the white light, and the first parameter is a ratio W/(R+G) of the first special observation image data W and the sum R+G.

Aspect 6

The endoscope system according to aspect 2, wherein the light source apparatus is configured to emit first special light that has a different wavelength region from white light, and is absorbed by the biological tissue differently according to the first feature amount, the color image data X is first special observation image data W obtained by imaging the biological tissue illuminated by the first special light, the color image data Y is a sum $\beta R+\gamma G$ obtained by using a coefficient $\beta$ and a coefficient $\gamma$ that are set in advance to perform weighted addition on first normal observation image data R and second normal observation image data G that are respectively an R component and a G component of normal observation image data in an RGB color space obtained by imaging the biological tissue illuminated by the white light, and the first parameter is a ratio $W/(\beta R+\gamma G)$ of the first special observation image data W and the sum $\beta R+\gamma G$.

In this case, it is preferable that the coefficient $\beta$ and the coefficient $\gamma$ are obtained in advance by preliminary experimentation performed using a sample having a known first feature amount. In other words, before usage of the endoscope system starts, it is preferable that the processor performs preliminary experimentation using the known sample to determine the coefficient $\beta$ and the coefficient $\gamma$ and store them.

Aspect 7

The endoscope system according to any one of aspects 3 to 6, wherein the imaging unit includes an R color filter configured to filter light into an R wavelength region in the RGB color space before the light is received by the image sensor, and the first normal observation image data R is data of an image captured via the R color filter of the image sensor.

Aspect 8

The endoscope system according to any one of aspects 3 to 7, wherein the light source apparatus includes:

a white light source that emits white light; and a first optical filter configured to obtain the first special light from the white light, and the light source apparatus switches between emitting the white light and the first special light.

Aspect 9

The endoscope system according to any one of aspects 1 to 8, wherein the processor includes a storage unit that stores data expressing a quantitative relationship between the first parameter and the first feature amount, and the first feature amount acquisition unit is configured to obtain the first feature amount by referencing the data expressing the quantitative relationship.

Aspect 10

The endoscope system according to any one of aspects 1 to 9, wherein the first feature amount is a total hemoglobin amount.

Aspect 11

The endoscope system according to any one of aspects 3 to 9, wherein the first feature amount is a total hemoglobin amount, and the first special observation image data W is data regarding the same wavelength region as a G wavelength region in the RGB color space.

Aspect 12

The endoscope system according to aspect 11, wherein the imaging unit includes a G color filter configured to filter light into a G wavelength region in the RGB color space before the light is received by the image sensor, and the first special observation image data W is data of an image captured by the image sensor via the G color filter.

Aspect 13

The endoscope system according to any one of aspects 1 to 12, wherein the processor includes:

a second parameter generation unit configured to generate a second parameter that has sensitivity to a second feature amount of the biological tissue but does not have sensitivity to the light scattering based on the color image data; and a second feature amount acquisition unit configured to acquire the second feature amount based on the first feature amount and the second parameter.

Aspect 14

The endoscope system according to any one of aspects 3 to 8, wherein the feature amount acquisition unit includes:

a second parameter generation unit configured to generate second parameter that has sensitivity to a second feature amount of the biological tissue but does not have sensitivity to the light scattering based on the color image data; and a second feature amount acquisition unit configured to acquire the second feature amount based on the first feature amount and the second parameter, the light source apparatus is configured to emit second special light that has a different wavelength region from white light, and is absorbed by the biological tissue differently according to the second feature amount, and the second parameter is a ratio N/W of second special observation image data N obtained by imaging the biological tissue illuminated by the second special light and first special observation image data W obtained by imaging the biological tissue illuminated by the first special light.

Aspect 15

The endoscope system according to aspect 14, wherein a wavelength region of the first special light is set such that absorption of the first special light by the biological tissue is dependent on the first feature amount but not dependent on the second feature amount.

Aspect 16

The endoscope system according to aspect 15, wherein a wavelength region of the second special light is set such that absorption of the second special light by the biological tissue is dependent on both the first feature amount and the second feature amount.

Aspect 17

The endoscope system according to any one of aspects 13 to 16, wherein the second feature amount is a degree of oxygen saturation.

Aspect 18

The endoscope system according to aspect 17, wherein the second special observation image data N is image data regarding the same wavelength region as a G wavelength region in the RGB color space.

Aspect 19

The endoscope system according to aspect 18, wherein the imaging unit includes a G color filter configured to filter light into a G wavelength region in the RGB color space before the light is received by the image sensor, and the second special observation image data N is data of an image captured via the G color filter.

Aspect 20

The endoscope system according to any one of aspects 1 to 19, including a feature amount distribution image generation unit configured to generate a feature amount distribution image that expresses a distribution of the first feature amount in the biological tissue based on the first feature amount.

Aspect 21

The endoscope system according to any one of aspects 13 to 19, including a feature amount distribution image generation unit configured to generate a feature amount distribution image that expresses a distribution of the second feature amount in the biological tissue based on the second feature amount.

Another aspect of the present invention is an analyzing apparatus, which includes the following aspects.

An analyzing apparatus including:

a light source apparatus;

an imaging unit including an image sensor configured to generate color image data by imaging biological tissue illuminated by light emitted by the light source apparatus; and a processor that has a first parameter generation unit configured to generate a first parameter that has sensitivity to a first feature amount of the biological tissue but does not have sensitivity to light scattering by the biological tissue based on the color image data, and a first feature amount acquisition unit configured to acquire the first feature amount based on the first parameter.

Advantageous Effects of Invention

According to the endoscope system and the analyzing apparatus described above, error arising from scattering is reduced, and more precise spectroscopic analysis can be performed.

BRIEF DESCRIPTION OF DRAWINGS

FIG. 11A shows an example of two-dimensional display of a degree of oxygen saturation distribution image, and FIG. 11B shows an example of three-dimensional display of a degree of oxygen saturation distribution image.

DESCRIPTION OF EMBODIMENTS

Figure 1:
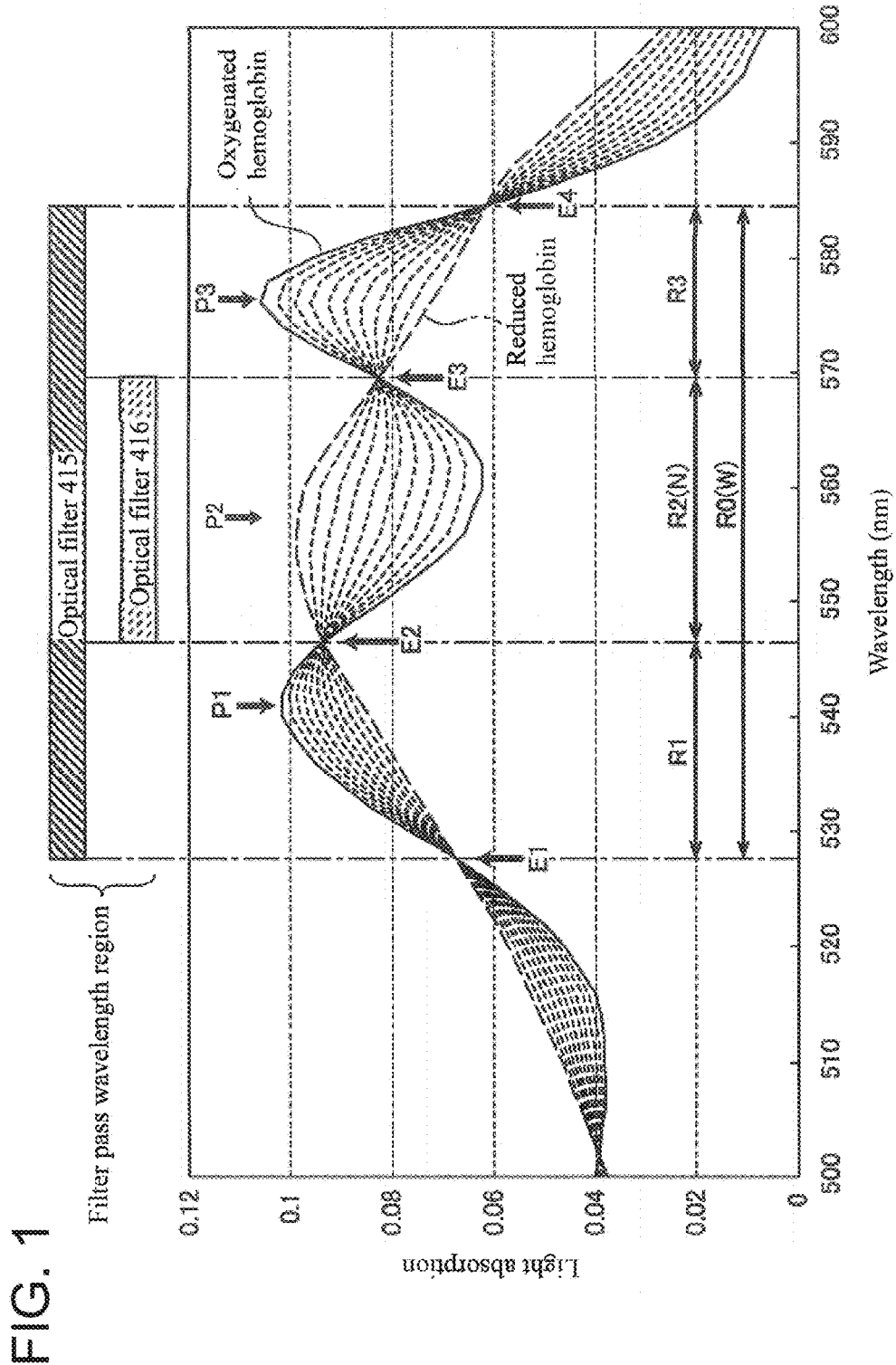
FIG. 1 shows the Q band absorption spectrum of hemoglobin.

Hereinafter, an embodiment of the present invention will be described with reference to the drawings.

An endoscope system (also called an endoscope apparatus hereinafter) of the present embodiment described below is a system for quantitatively analyzing biological information of a subject (e.g., a feature amount of biological tissue such as the total hemoglobin amount or the degree of oxygen saturation) based on image data of an image of an imaging subject that has light components in different wavelength regions, and for converting the analysis results into an image and displaying the image. In order to acquire the image data, an image of biological tissue may be captured by receiving light separated into a predetermined wavelength region in order to be able to calculate biological information, but in order to acquire precise image data with little noise, it is preferable to enhance components in different wavelength regions by capturing an image of biological tissue that is illuminated by multiple types of light in different predetermined wavelength regions.

The spectral characteristics of blood (i.e., the spectral characteristics of hemoglobin) have a property of continuously varying according to the total hemoglobin amount and the degree of oxygen saturation, and this property is used in the quantitative analysis of the total hemoglobin amount and the degree of oxygen saturation described below.

In the present specification, "R" in the R component in an image or image data, R pixels, the R color filter in the color filter, and the like is R (red) in the RGB color space, and refers to a wavelength region in the wavelength region of 570 nm or more within the range of 360 to 830 nm, which is the range of the visible wavelength region of light, and refers to a wavelength region of 580 to 700 nm for example. Also, "G" in the G component in an image or image data, G pixels, the G color filter in the color filter, and the like is G (green) in the RGB color space, and refers to a wavelength region in the wavelength region of 470 to 620 nm, for example, within the range of 360 to 830 nm, which is the range of the visible wavelength region of light. "B" in the B component in an image or image data, B pixels, the B color filter in the color filter, and the like is B (blue) in the RGB color space, and refers to a wavelength region in the wavelength region of 530 nm or lower within the range of 360 to 830 nm, which is the range of the visible wavelength region of light, and refers to the wavelength region of 420 to 520 nm for example. There are also cases where "R", "G", and "B" on their own refer to the pixel values of R pixels, G pixels, and B pixels in an image.

White light is not strictly limited to light that includes all of the wavelength components of visible light, and may be light that includes components in the above-described R, G, and B wavelength regions, for example.

Spectral Characteristics of Biological Tissue and Principle of Calculation of Biological Information Before giving a description of the detailed configuration of the endoscope apparatus according to the present embodiment, the following describes the spectral characteristics of hemoglobin and the principle of the calculation of a feature amount of biological tissue (biological information), such as the degree of oxygen saturation, according to the present embodiment.

FIG. 1 shows the absorption spectrum of hemoglobin at roughly 550 nm. Hemoglobin has a strong absorption band at roughly 550 nm that is called the Q band and derives from porphyrin. The absorption spectrum of hemoglobin varies according to the degree of oxygen saturation. The degree of oxygen saturation is the percentage of oxygenated hemoglobin HbO in the total amount of hemoglobin. The solid line waveform in FIG. 1 is the absorption spectrum of oxygenated hemoglobin HbO in the case where the degree of oxygen saturation is 100%, and the long dashed line waveform is the absorption spectrum in the case where the degree of oxygen saturation is 0%, that is to say the absorption spectrum of reduced hemoglobin Hb. Also, the short dashed lines are the absorption spectrums of hemoglobin (mixture of oxygenated hemoglobin HbO and reduced hemoglobin Hb) at intermediate degrees of oxygen saturation (10, 20, 30, . . . 90%).

As shown in FIG. 1, in the Q band, oxygenated hemoglobin HbO and reduced hemoglobin Hb have mutually different peak wavelengths. Specifically, oxygenated hemoglobin HbO has an absorption peak P1 at a wavelength of roughly 542 nm and an absorption peak P3 at a wavelength of roughly 576 nm. On the other hand, reduced hemoglobin Hb has an absorption peak P2 at roughly 556 nm. FIG. 1 shows a two-component absorption spectrum in which the sum of the concentrations of the respective components (oxygenated hemoglobin HbO and reduced hemoglobin Hb) is constant, and therefore isosbestic points E1, E2, E3, and E4, at which the absorption is constant regardless of the concentrations of the respective components (i.e., the degree of oxygen saturation), appear in the spectrum. In the following description, the wavelength region sandwiched between the isosbestic points E1 and E2 will be called a wavelength region R1, the wavelength region sandwiched between the isosbestic points E2 and E3 will be called a wavelength region R2, and the wavelength region sandwiched between the isosbestic points E3 and E4 will be called a wavelength region R3. Also, the wavelength region sandwiched between the isosbestic points E1 and E4 (i.e., the combination of the wavelength regions R1, R2, and R3) will be called a wavelength region R0. Also, in the following description, the wavelength region R2 is also called the N band (Narrow-band), and the wavelength region R0 is also called the W band (Wide-band).

In this way, the wavelength region R0 and the wavelength region R2 are determined based on a wavelength region that has points where the absorption is constant regardless of the degree of oxygen saturation, and that has regions where the absorption varies according to the degree of oxygen saturation. Although there are no particular limitations on the ranges of the wavelength region R0 and the wavelength region R2, it is preferable that they are determined based on regions in which variation according to the degree of oxygen saturation is high. For example, the W band is preferably the range of 500 nm to 600 nm, or more preferably the range of 520 nm to 590 nm. Also, the N band is within the range of the W band, is narrower than the W band, and is preferably the range of 520 nm to 590 nm, or more preferably the range of 540 nm to 580 nm, for example.

As shown in FIG. 1, in the wavelength regions between adjacent isosbestic points, the absorption of hemoglobin increases or decreases linearly relative to the degree of oxygen saturation.

Specifically, integrated values AR1 and AR3 of the absorption of hemoglobin in the wavelength regions R1 and R3 linearly increase relative to the concentration of oxygenated hemoglobin. Also, an integrated value AR2 of the absorption of hemoglobin in the wavelength region R2 linearly increases relative to the concentration of reduced hemoglobin.

Here, the degree of oxygen saturation is defined by Expression 1 below.

$$Sat = \frac{[HbO]}{[Hb] + [HbO]} \qquad \text{Expression 1}$$

where
Sat: degree of oxygen saturation
[Hb]: concentration of reduced hemoglobin
[HbO]: concentration of oxygenated hemoglobin
[Hb]+[HbO]: total hemoglobin amount (tHb)

Also, Expression 2 and Expression 3 that express the concentrations of oxygenated hemoglobin HbO and reduced hemoglobin Hb are obtained from Expression 1.

$$[HbO] = Sat \cdot ([Hb] + [HbO]) \qquad \text{Expression 2}$$

$$[Hb] = (1 - Sat) \cdot ([Hb] + [HbO]) \qquad \text{Expression 3}$$

Accordingly, the integrated values AR1, AR2, and AR3 of the absorption of hemoglobin are characteristic values that are dependent on both the degree of oxygen saturation Sat and the total hemoglobin amount tHb.

Also, through research carried by the applicant of this patent application, it was found that an integrated value AR0 of the absorption of hemoglobin in the wavelength region R0, which is made up of the wavelength regions R1, R2, and R3, is a value that is not dependent on the degree of oxygen saturation Sat, but varies according to the total hemoglobin amount tHb.

Accordingly, the total hemoglobin amount tHb can be determined based on the absorption integrated value AR0. Also, the degree of oxygen saturation Sat can be determined based on the absorption integrated values AR1, AR2, and AR3, and the total hemoglobin amount tHb determined based on the absorption AR0. Note that as shown in FIG. 1, the amount of variation of the absorption integrated value according to the degree of oxygen saturation Sat in the wavelength regions R1, R2, and R3, that is to say the area of the region enclosed by the solid-line waveform and the long-dash waveform in FIG. 1, is the largest in the wavelength region R2 among the wavelength regions R0 to R3, and the integrated value AR2 of absorption in the wavelength region R2 is the characteristic amount that is most sensitive to the degree of oxygen saturation Sat. In the embodiment described later, the degree of oxygen saturation Sat is determined using light in the wavelength region R2 (N band).

Next, the influence of scattering on the spectral characteristics of biological tissue will be described.

Figure 2A:
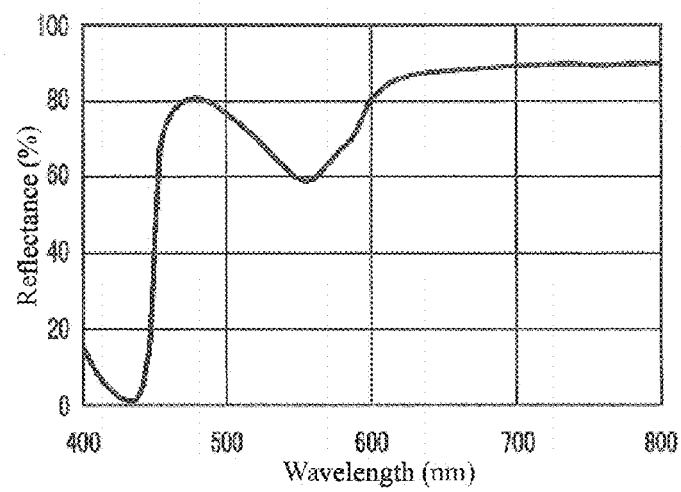
FIG. 2A to 2C are diagrams, each showing an example of results of simulation of the spectral characteristics of biological tissue.
Figure 2B:
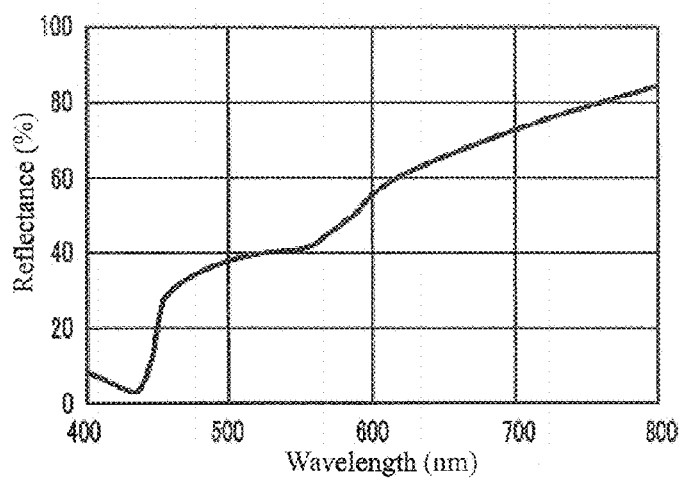
Figure 2C:
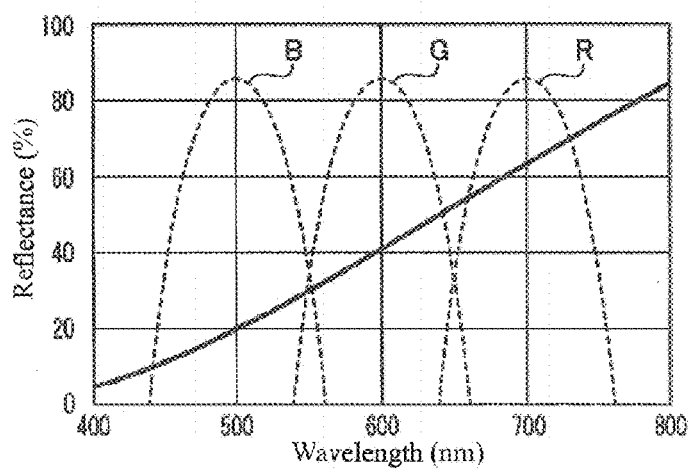

FIG. 2A to 2C show examples of a reflection spectrum that indicates the spectral characteristics of biological tissue in the visible light region obtained by simulation calculation, and show the influence of light scattering on spectral characteristics. In the graphs in FIG. 2A to 2C, the horizontal axis indicates the wavelength, and the vertical axis indicates the reflectance. The reflection spectrum of biological tissue such as a digestive track wall is influenced by not only the absorption characteristics of the components that make up the biological tissue, specifically the absorption spectrum characteristics of oxygenated hemoglobin and reduced hemoglobin, but also the wavelength characteristics of light scattering by biological tissue. FIG. 2A shows the reflection spectrum in the case of no light scattering whatsoever, FIG. 2C shows the reflection spectrum in the case where there is no absorption whatsoever by hemoglobin, and light scattering occurs, and FIG. 2B shows the reflection spectrum in the case where the contribution of light scattering by biological tissue (light attenuation caused by scattering) and the contribution of hemoglobin absorption (light attenuation caused by absorption) on the reflection spectrum are approximately the same.

As shown in FIG. 2A to 2C, the biological tissue spectral characteristics vary according to the intensity of light scattering, and therefore if biological information such as the degree of oxygen saturation Sat is calculated based on the biological tissue spectral characteristics without giving consideration to the extent of light scattering, the biological information can change in value according to the intensity of light scattering. In other words, if the biological tissue spectral characteristics (e.g., reflectance in the wavelength region R2) are used as-is to calculate the biological information, a calculation result that contains error arising from light scattering will be obtained. In order to obtain a precise analysis result, it is necessary to correct the error arising from light scattering.

Methods of correcting error arising from light scattering include a method of correcting error after calculating biological information such as the degree of oxygen saturation Sat based on biological tissue spectral characteristics, and a method of generating an intermediate parameter that is not dependent on light scattering based on biological tissue spectral characteristics, removing the component that is dependent on light scattering at the stage of generating the intermediate parameter, and then calculating biological information based on the correlation relationship between the intermediate parameter and the biological information, that is to say a biological tissue feature amount. In the present embodiment, the latter method is used to acquire biological information that does not contain error arising from light scattering. In order to realize this method, the inventor of the present invention searched for a parameter that has high sensitivity to (is highly correlated with) biological information that is to be acquired, such as the total hemoglobin amount tHb or the degree of oxygen saturation Sat that are biological tissue feature amounts, and also has almost no sensitivity to light scattering.

Figure 3:
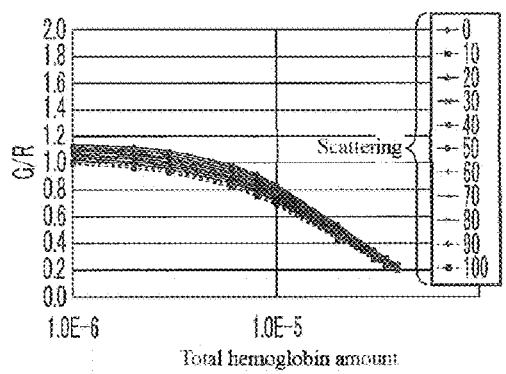
FIG. 3 includes graphs showing examples of the correlation between various parameters and biological information.
Figure 3:
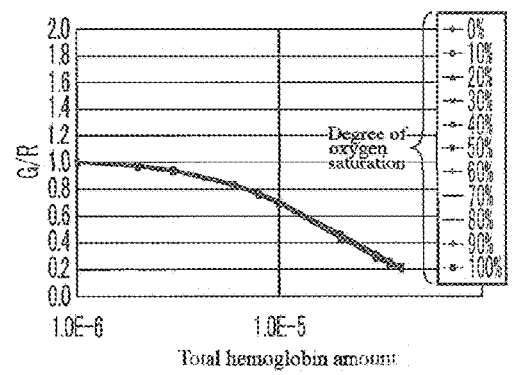
Figure 3:
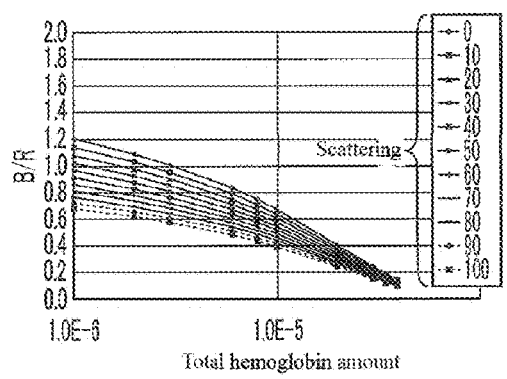
Figure 3:
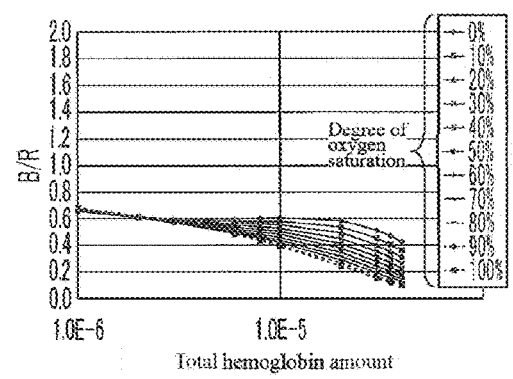
Figure 3:
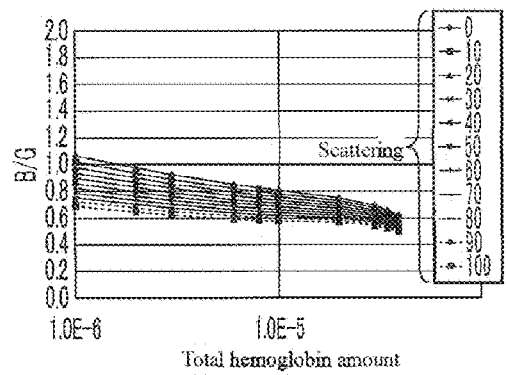
Figure 3:
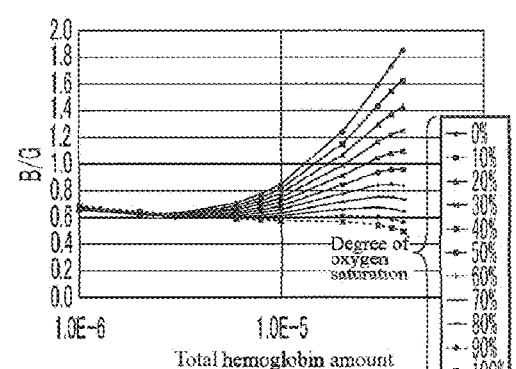
Figure 4:
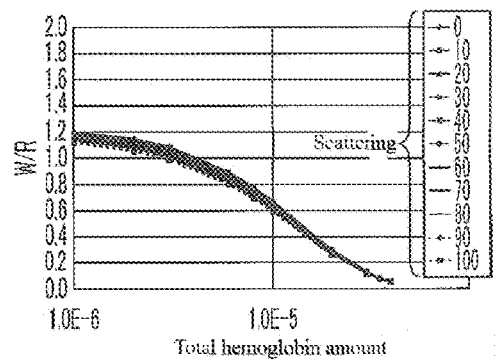
FIG. 4 includes graphs showing examples of the correlation between various parameters and biological information.
Figure 4:
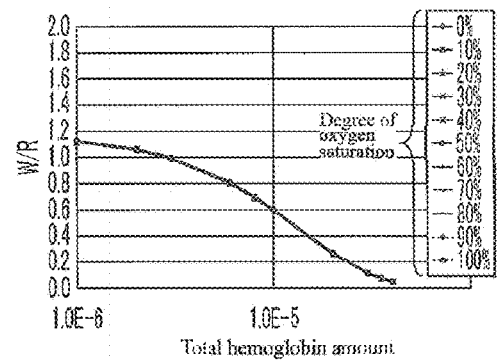
Figure 4:
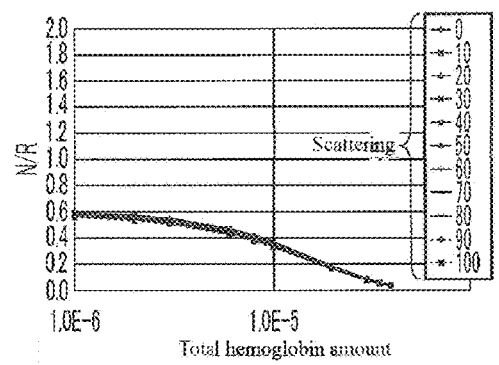
Figure 4:
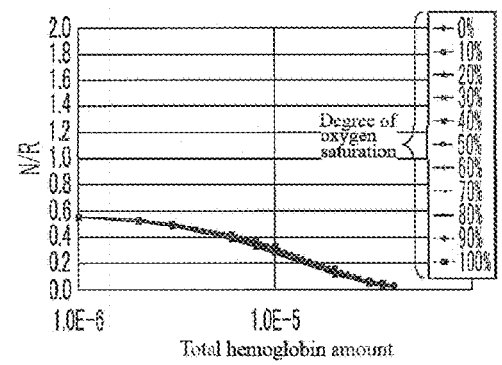
Figure 4:
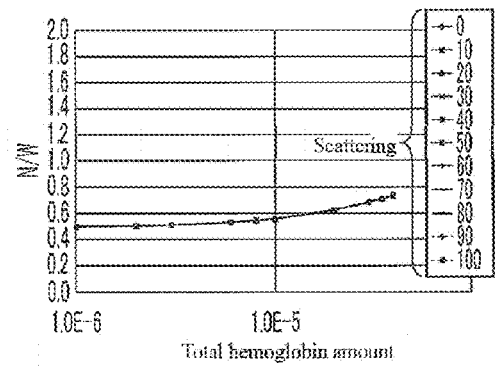
Figure 4:
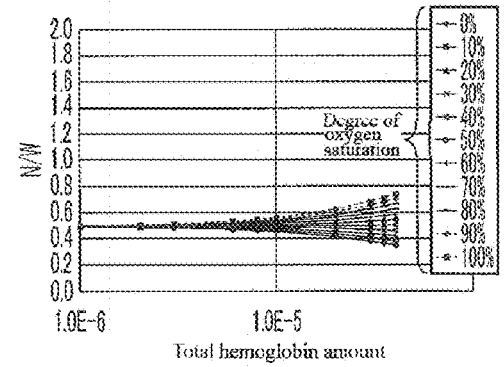
Figure 5:
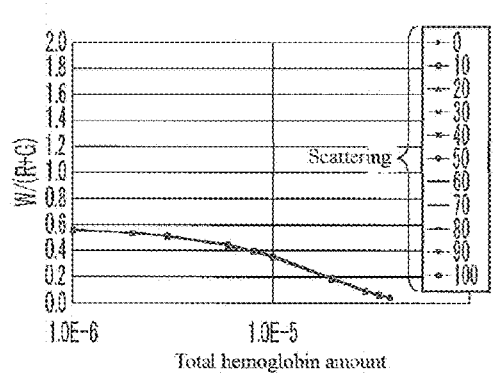
FIG. 5 includes graphs showing examples of the correlation between various parameters and biological information.
Figure 5:
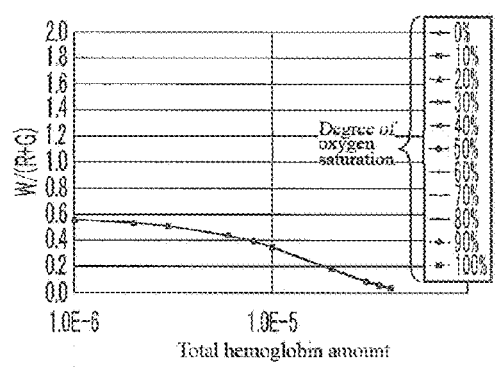

FIGS. 3 to 5 are graphs showing examples of the correlation between various parameters that can be acquired from endoscopic image data and the total hemoglobin amount tHb and the degree of oxygen saturation Sat, and these graphs are plots of simulation results of the parameters. The horizontal axis in the graphs indicates the total hemoglobin amount tHb, and the vertical axis indicates parameter values. Also, Table 1 is an organized arrangement of elements in the graphs of FIGS. 3 to 5.

Note that "sensitivity" in Table 1 is indicated using one to three stars representing the sensitivity (i.e., magnitude of variation range) of the parameters relative to change in the total hemoglobin amount tHb, the intensity of light scattering, and the degree of oxygen saturation Sat, as interpreted from the graphs of FIGS. 3 to 5. A larger number of stars indicates higher parameter sensitivity, that is to say indicates a larger variation range.

TABLE 1

| Graph | | Parameter | Setting | | Sensitivity | | |
|---|---|---|---|---|---|---|---|
| | | | Contribution of scattering | Degree of oxygen saturation | Total hemoglobin amount | Scattering | Degree of oxy. saturation |
| FIG. 3 | (A1) | G/R | 0~100 | 100% | ★★★ | ★★ | |
| | (A2) | | 0 | 0~100% | | | ★ |
| | (B1) | B/R | 0~100 | 100% | ★★ | ★★★ | |
| | (B2) | | 0 | 0~100% | | | ★★ |
| | (C1) | B/G | 0~100 | 100% | ★★ | ★★ | |
| | (C2) | | 0 | 0~100% | | | ★★★ |
| FIG. 4 | (D1) | W/R | 0~100 | 100% | ★★★ | ★ | |
| | (D2) | | 0 | 0~100% | | | ★ |
| | (E1) | N/R | 0~100 | 100% | ★★ | ★ | |
| | (E2) | | 0 | 0~100% | | | ★ |
| | (F1) | N/W | 0~100 | 100% | ★ | ★ | |
| | (F2) | | 0 | 0~100% | | | ★★ |
| FIG. 5 | (G1) | W/(R + G) | 0~100 | 100% | ★★ | ★ | |
| | (G2) | | 0 | 0~100% | | | ★ |

Graphs (A1) and (A2) in FIG. 3 are graphs plotting simulation results for the parameter "G/R". "G" is the pixel value of G pixels (pixels provided with the green G color filter) obtained by normal observation performing using white light as illumination light for the biological tissue. Also, "R" is the pixel value of R pixels (pixels provided with the red R color filter) obtained by normal observation. The parameter "G/R," is the result of dividing the pixel value G obtained by normal observation by the pixel value R. Normal observation refers to imaging biological tissue using later-described white light WL, and acquiring an image that has an R component, a G component, and a B component in the RGB color space.

Note that in the present specification, pixel values are not limited to pixel values of an imaging signal (so-called RAW data) from an image sensor that includes an RGB primary color filter, and also include pixel values of image data obtained by performing various types of image processing such as demosaic processing (interpolation processing) and linear matrix processing on an imaging signal. For example, later-described processing can also be performed using R pixel values, G pixel values, and B pixel values that are the values of pixels included in image data that has an R component, a G component, and a B component in the RGB color space obtained by performing demosaic processing and color space conversion processing on an imaging signal from an image sensor that includes a complementary color filter.

Graphs (B1) and (B2) in FIG. 3 are graphs plotting simulation results for the parameter "B/R". Also, "B" is the pixel value of B pixels (pixels provided with the blue B color filter) obtained by normal observation performed using white light WL. The parameter "B/R" is the result of dividing the pixel value B obtained by normal observation by the pixel value R.

Graphs (C1) and (C2) in FIG. 3 are graphs plotting simulation results for the parameter "B/G". The parameter "B/G" is the result of dividing the pixel value B obtained by normal observation by the pixel value G.

Graphs (D1) and (D2) in FIG. 4 are graphs plotting simulation results for the parameter "W/R". "W" is the pixel value of G pixels obtained by special observation performed using illumination light in the wavelength region R0 (W band) shown in FIG. 1. Note that as will be described later, the wavelength region R0 is included in a wavelength region in which G pixels of the image sensor have sensitivity. The parameter "W/R" is the result of the pixel value W of G pixels obtained by special observation performed using illumination light in the W band being divided by the pixel value R obtained by normal observation.

Graphs (E1) and (E2) in FIG. 4 are graphs plotting simulation results for the parameter "N/R". "N" is the pixel value of G pixels obtained by special observation performed using illumination light in the wavelength region R2 (N band) shown in FIG. 1. The parameter "N/R" is the result of the pixel value N of G pixels obtained by special observation performed using illumination light in the N band being divided by the pixel value R obtained by normal observation.

Graphs (F1) and (F2) in FIG. 4 are graphs plotting simulation results for the parameter "N/W". The parameter "N/W" is the result of the pixel value N of G pixels obtained by special observation performed using illumination light in the N band being divided by the pixel value W of G pixels obtained by special observation performed using illumination light in the W band.

Graphs (G1) and (G2) in FIG. 5 are graphs plotting simulation results for the parameter "W/(R+G)". The parameter "W/(R+G)" is the result of the pixel value W of G pixels obtained by special observation performed using illumination light in the W band being divided by the sum "R+G" of the pixel value R of R pixels and the pixel value G of G pixels obtained by normal observation performed using white light WL as illumination light.

Also, the graphs (A1), (B1), (C1), (D1), (E1), (F1), and (G1) on the left side in FIGS. 3 to 5 are graphs in which the degree of oxygen saturation Sat is fixed at 100%, and the contribution of light scattering (parameter indicating the intensity of light scattering) is varied between 0 and 100 in units of 10 and plotted in an overlapped manner. Based on these graphs, it is possible to find out the degree of sensitivity of the parameters to light scattering.

Also, the graphs (A2), (B2), (C2), (D2), (E2), (F2), and (G2) on the right side in FIGS. 3 to 5 are graphs in which the contribution of scattering is set to 0, and the degree of oxygen saturation Sat is varied between 0 and 100% in units of 10% and plotted in an overlapped manner. Based on these graphs, it is possible to find out the degree of sensitivity of the parameters to the degree of oxygen saturation Sat.

As shown in Table 1 and the graphs (D1) and (D2) in FIG. 4, the parameter "W/R" has high sensitivity to the total hemoglobin amount tHb, but has almost no sensitivity to light scattering or the degree of oxygen saturation Sat. For this reason, the value of the total hemoglobin amount tHb is uniquely determined by the value of the parameter "W/R". In other words, an accurate total hemoglobin amount tHb that is not dependent on light scattering or degree of oxygen saturation Sat can be obtained based on the value of the parameter "W/R" obtained from image data and the quantitative relationship between the total hemoglobin amount tHb and the parameter "W/R" shown in the graphs (D1) and (D2).

Also, as shown in Table 1 and the graphs (F1) and (F2) in FIG. 4, the parameter "N/W" has high sensitivity to the degree of oxygen saturation Sat, but has almost no sensitivity to light scattering. For this reason, if the total hemoglobin amount tHb is known, the value of the degree of oxygen saturation Sat can be uniquely determined based on the value of the parameter "N/W" according to the graph (F2). Specifically, if the plotted point in the graph (F2) that most closely conforms to the numerical value pair of the value of the total hemoglobin amount tHb and the value of the parameter "N/W" obtained from the pixel values is selected, the value of the degree of oxygen saturation Sat corresponding to the plotted point is used as the degree of oxygen saturation Sat of the biological tissue appearing at that pixel. Note that the value of the total hemoglobin amount tHb is obtained based on the value of the parameter "W/R" obtained from the image data and the relationship between the total hemoglobin amount tHb and the parameter "W/R" indicated in the graphs (D1) and (D2).

Also, as shown in Table 1 and the graphs (G1) and (G2) in FIG. 5, similarly to the parameter "W/R" described above, the parameter "W/(R+G)" (i.e., the ratio W/(R+G)) has sensitivity to the total hemoglobin amount tHb, but has almost no sensitivity to light scattering or degree of oxygen saturation Sat, and therefore an accurate value of the total hemoglobin amount tHb that is not dependent on light scattering or the degree of oxygen saturation Sat is obtained based on the quantitative relationship between the total hemoglobin amount tHb and the parameter "W/(R+G)" shown in the graphs (G1) and (G2).

As described above, by performing simple calculation using the relationships shown in the graphs (D1) and (D2) or the graphs (G1) and (G2), along with the relationship shown in the graph (F2) or (C2), it is possible to obtain accurate values for the total hemoglobin amount tHb and the degree of oxygen saturation Sat that contain almost no error arising from scattering. Hereinafter, the parameter W/R, the parameter W/(R+G), the parameter N/W, and the like will be called the ratio W/R, the ratio W/(R+G), the ratio N/W, and the like.

Note that the numerator "W" in "W/R" and "W/(R+G)" in the graph (D1) in FIG. 4 and the graph (G1) in FIG. 5 is a pixel value in an image captured using illumination light in the wavelength region R0 (W band) so as to reflect the integrated value AR0 of the absorption of hemoglobin that is not dependent on the degree of oxygen saturation Sat but varies according to the total hemoglobin amount tHb as described above, and therefore "W" is a value that is not dependent on the degree of oxygen saturation Sat but varies according to the total hemoglobin amount tHb. This "W" is influenced by light scattering as shown in FIG. 2B. However, as shown in the graph (D1) or the graph (G1), "W/R" or "W/(R+G)" is not influenced by light scattering, and therefore the denominator "R" or "(R+G)" in "W/R" or "W/(R+G)" has information indicating the extent of light scattering.

Accordingly, the numerator "W" in "W/R" or "W/(R+G)" is image data of an image that has a component in a wavelength region that has sensitivity to the total hemoglobin amount tHb of biological tissue and has sensitivity to light scattering by biological tissue, and the denominator "R" or "(R+G)" is image data of an image that has a component in a wavelength region that does not have sensitivity to the total hemoglobin amount tHb of biological tissue but is sensitive to light scattering by biological tissue. Image data of an image that has a component in a predetermined wavelength region refers to image data of an image formed by light that has a component in the predetermined wavelength region. For this reason, based on the "W" image data and the "R" or "(R+G)" image data, it is possible to generate a parameter that has sensitivity to the total hemoglobin amount tHb but does not have sensitivity to light scattering by biological tissue.

Based on this finding, the total hemoglobin amount tHb and the degree of oxygen saturation Sat are calculated based on multiple pieces of image data below. The total hemoglobin amount tHb can be calculated using a numerical value table T1 (or function) that expresses the quantitative relationship between the total hemoglobin tHb and the parameter W/R, and the total hemoglobin amount tHb can be calculated based on the ratio W/R of biological tissue with reference to this numerical value table T1. Also, the total hemoglobin amount tHb can be calculated using a numerical value table T1 (or function) that expresses the quantitative relationship between the total hemoglobin tHb and the parameter W/(R+G), and the total hemoglobin amount tHb can be calculated based on the ratio W/(R+G) of biological tissue with reference to this numerical value table T1. The degree of oxygen saturation Sat can be calculated using a numerical value table T2 (or function) that expresses the quantitative relationship between the total hemoglobin amount tHb, the parameter N/W, and the degree of oxygen saturation Sat, and the degree of oxygen saturation Sat can be calculated based on the ratio N/W of biological tissue with reference to this numerical value table T2. As described above, the parameter N/W is a parameter that has sensitivity to the degree of oxygen saturation Sat of biological tissue (second feature amount), but does not have sensitivity to the total hemoglobin amount tHb (first feature amount) or light scattering.

Configuration of Endoscope Apparatus

Figure 6:
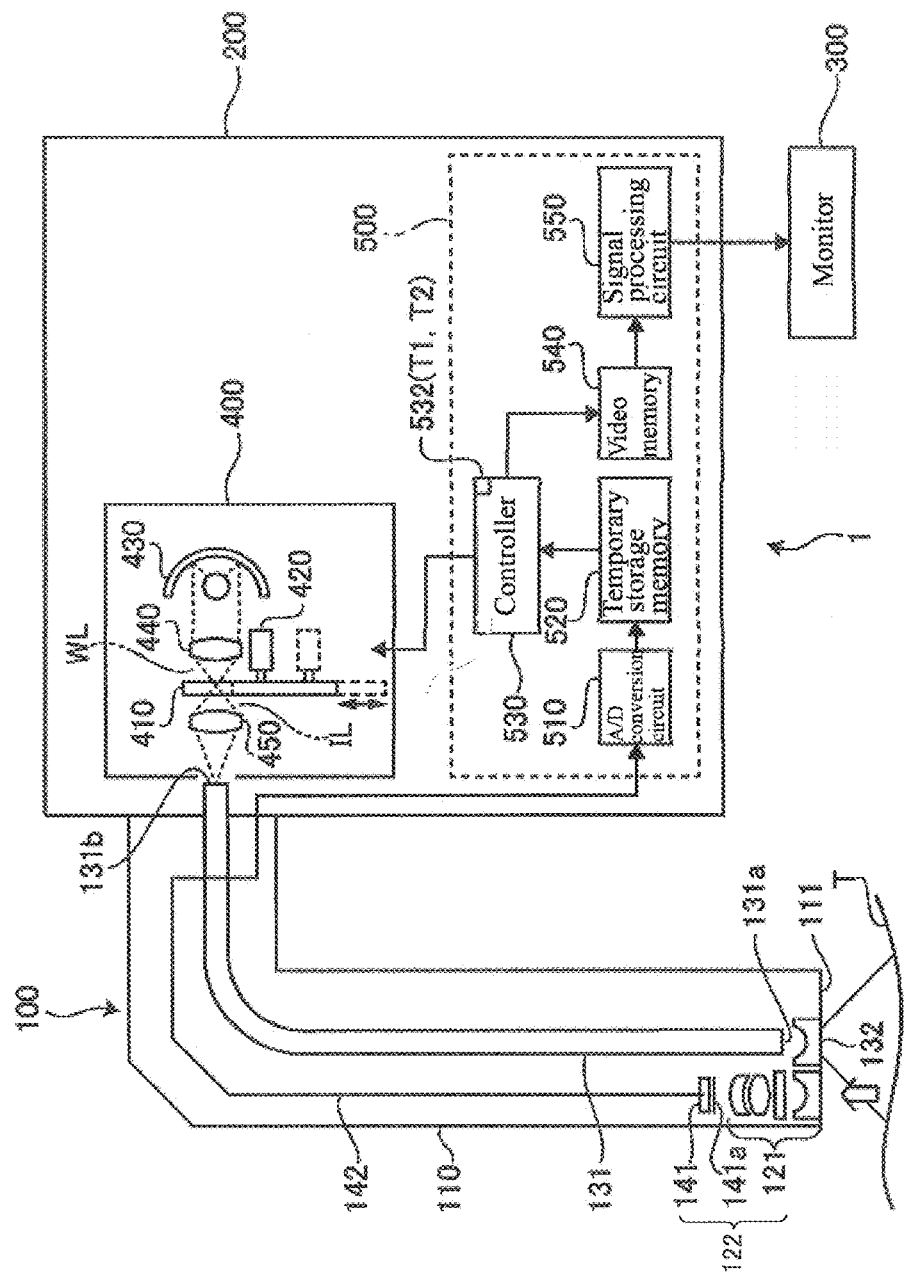
FIG. 6 is a block diagram showing an example of an endoscope system of an embodiment of the present invention.
Figure 7:
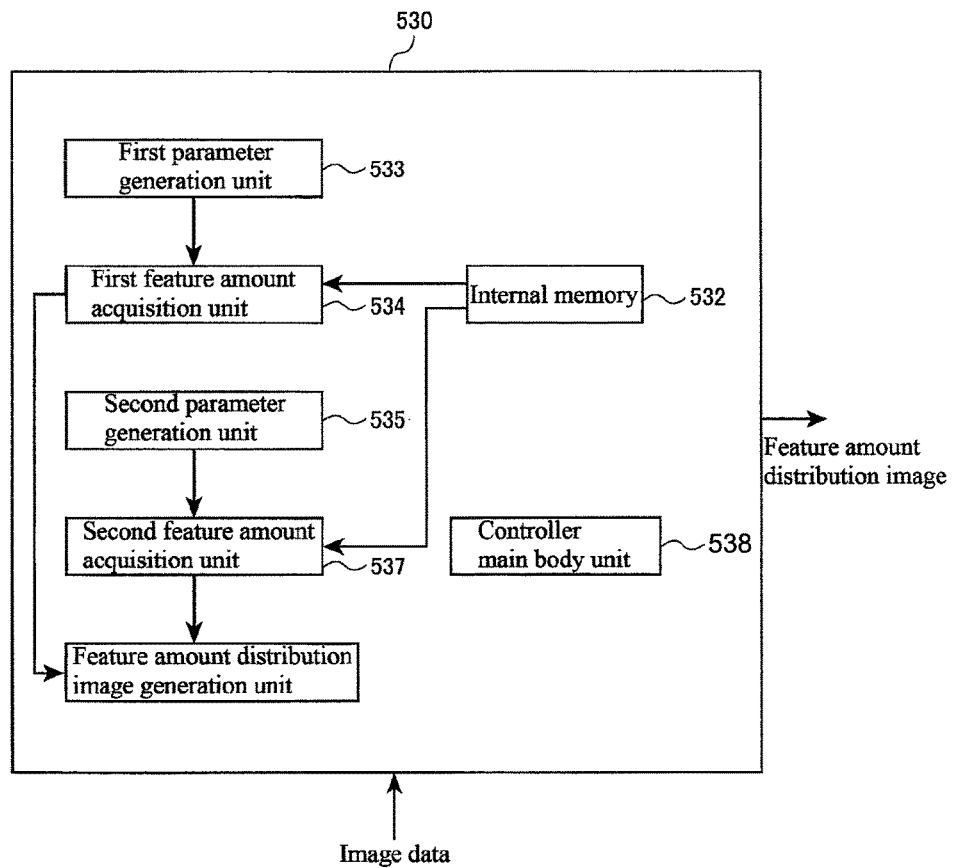
FIG. 7 is a block diagram illustrating an example of the configuration of a controller of the endoscope system shown in FIG. 6.

FIG. 6 is a block diagram showing an example of the configuration of an endoscope apparatus 1 according to the present embodiment. FIG. 7 is a block diagram illustrating an example of the configuration of a controller of the endoscope apparatus 1. The endoscope apparatus 1 of the present embodiment includes an electronic endoscope 100, a processor 200, and a monitor 300. The electronic endoscope 100 and the monitor 300 are detachably connected to the processor 200. Also, a light source unit 400 and an image processing unit 500 are built into the processor 200.

The electronic endoscope 100 has an insertion tube 110 for insertion into the subject's body. The electronic endoscope 100 is internally provided with a light guide 131 that extends over approximately the entire length thereof. One end portion (distal end portion 131a) of the light guide 131 is arranged in the distal end portion of the insertion tube 110 (insertion tube distal end portion 111), and the other end portion (base end portion 131b) of the light guide 131 is connected to the processor 200. The processor 200 includes a light source unit 400 that includes a light source lamp 430 or the like for generating high-intensity white light WL, such as a xenon lamp, and the illumination light IL generated by the light source unit 400 enters the base end 131b of the light guide 131. Light that enters the base end 131b of the light guide 131, passes through the light guide 131 and is guided to the distal end portion 131a thereof, and is then emitted from the distal end portion 131a. A light distribution lens 132 arranged opposing the distal end portion 131a of the light guide 131 is provided at the insertion tube distal end portion 111 of the electronic endoscope 100, and illumination light IL emitted from the distal end portion 131a of the light guide 131 passes through the light distribution lens 132 and illuminates biological tissue T in the vicinity of the insertion tube distal end portion 111.

Also, the insertion tube distal end portion 111 is provided with an objective optical system 121 and an image sensor 141. Part of the illumination light IL reflected or scattered by the surface of the biological tissue T (returning light) enters the objective optical system 121, is condensed, and forms an image on the light receiving surface of the image sensor 141. The image sensor 141 of the present embodiment is a CCD (Charge Coupled Device) image sensor for color image capturing, and includes a color filter 141a on its light receiving surface. Another type of image sensor such as a CMOS (Complementary Metal Oxide Semiconductor) image sensor may be used as the image sensor 141. The objective optical system 121, the color filter 141a, and the image sensor 141 configure an imaging unit 122.

Figure 8:
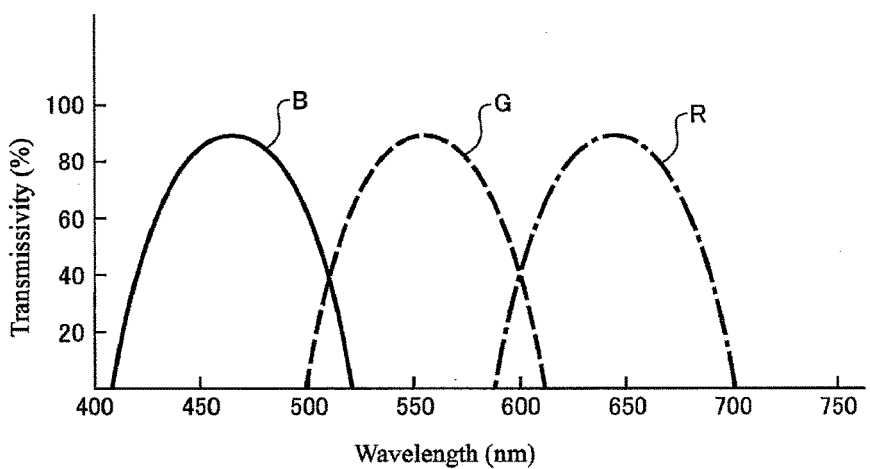
FIG. 8 is a diagram showing an example of the transmission spectrum of color filters included in an image sensor.

The color filter 141a includes an array of R color filters that allow red light to pass, G color filters that allow green light to pass, and B color filters that allow blue light to pass, and is a so-called on-chip filter that is formed directly on the light receiving element of the image sensor 141. In other words, the color filter 141a is configured to filter light into the R, G, and B wavelength regions in the RGB color space before the light is received by the image sensor 141. The R, G, and B filters have the spectral characteristics shown in FIG. 8. FIG. 8 is a diagram showing an example of the transmission spectrum of the color filter included in the image sensor 141. The R color filters of the present embodiment are filters that allow light with a wavelength longer than approximately 570 nm to pass, the G color filters are filters that allow light with a wavelength of approximately 470 nm to 620 nm to pass, and the B color filters are filters that allow light with a wavelength shorter than approximately 530 nm to pass.

The image sensor 141 is controlled to operate in synchronization with an image processing unit 500 that will be described later, and periodically (e.g., at intervals of 1/30 second) outputs an imaging signal that corresponds to an image of biological tissue formed on the aught receiving surface. The imaging signal output from the image sensor 141 is sent to the image processing unit 500 of the processor 200 via a cable 142.

The image processing unit 500 includes an A/D conversion circuit 510, a temporary storage memory 520, a controller 530, a video memory 540, and a signal processing circuit 550. The A/D conversion circuit 510 performs A/D conversion on an imaging signal received from the image sensor 141 of the electronic endoscope 100 via the cable 142, and outputs digital image data. The digital image data output from the A/D conversion circuit 510 is sent to and stored in the temporary storage memory 520. This digital image data includes R digital image data obtained by the light receiving elements on which the R color filters are mounted, G digital image data obtained by the light receiving elements on which the G color filters are mounted, and B digital image data obtained by the light receiving elements on which the B color filters are mounted.

The controller 530 processes one or more pieces of digital image data stored in the temporary storage memory 520 to generate screen data for display on the monitor 300, and sends the screen data to the video memory 540. For example, the controller 530 generates a reflection spectrum for the biological tissue T for each pixel (x,y) based on screen data generated based on image data showing the distribution of the total hemoglobin amount tHb of the biological tissue and image data showing the distribution of the degree of oxygen saturation Sat, based on screen data generated based on one piece of digital image data, based on screen data in which multiple pieces of digital image data are arranged side-by-side, or based on multiple pieces of digital image data, then uses the reflection spectrum to generate screen data that includes an image that shows healthy sites and lesion sites in different colors, or generate screen data that displays a graph of the reflection spectrum of the biological tissue T that corresponds to a certain pixel (x,y), and then stores the screen data in the video memory 540.

As shown in FIG. 7, the controller 530 includes an internal memory 532, a first parameter generation unit 533, a first feature amount acquisition unit 534, a second parameter generation unit 535, a second feature amount acquisition unit 536, a feature amount distribution image generation unit 537, and a controller main body unit 538.

The internal memory 532 stores digital image data obtained using various types of illumination light that will be described later, and also holds a numerical value table T1 (or function) that expresses the quantitative relationship between the total hemoglobin amount tHb and the above-described parameter W/R, and a numerical value table T2 (or function) that expresses the quantitative relationship between the total hemoglobin amount tHb, the above-described parameter N/W, and the degree of oxygen saturation Sat. This stored information is retrieved as necessary.

The first parameter generation unit 533 generates a parameter (first parameter) W/R value for each pixel based on color image data stored in the internal memory 532. The parameter W/R value is the ratio of pixel values at the same pixel position in first special observation image data W, which is obtained by the image sensor 141 imaging biological tissue using light in the wavelength region R0 (W band), and first normal observation image data R, which is the R component of normal observation image data in the RGB color space obtained by imaging biological tissue illuminated by white light WL. The wavelength region R0 is different from the wavelength region of white light WL, and is a wavelength region in which light absorption by biological tissue changes according to the total hemoglobin amount tHb (first feature amount). The first normal observation image data R is image data captured via the R color filter of the image sensor 141. As shown in the graphs (D1) and (D2) in FIG. 4, the parameter W/R is a parameter that has sensitivity to the total hemoglobin amount tHb of biological tissue, but does not have sensitivity to light scattering by biological tissue.

The first feature amount acquisition unit 534 acquires the total hemoglobin amount tHb based on the parameter W/R value. The first feature amount acquisition unit 534 obtains the total hemoglobin amount tHb for each pixel based on the parameter W/R value by retrieving and referencing the numerical value table T1 (or function) that expresses the quantitative relationship between the total hemoglobin amount tHb and the parameter W/R, which is held in the internal memory 532. Specifically, the first feature amount acquisition unit 534 acquires the total hemoglobin amount tHb (first feature amount) based on the parameter W/R. The parameter W/R is the ratio between the first special observation image data W, which is obtained by imaging biological tissue illuminated by first special light that has a different wavelength region from white light, and in which light absorption by biological tissue changes according to the total hemoglobin amount tHb (first feature amount), and the first normal observation image data R, which is the R component of normal observation image data in the RGB color space obtained by imaging biological tissue illuminated by white light.

Note that the first special observation image data W and the wavelength region of the image including the R component vary depending on the type of image sensor 141 and the filter characteristics of the color filter 141a, and the first special observation image data W and the wavelength region of the image including the R component also vary depending on error between apparatuses in the endoscope system 10 as well. For this reason, it is preferable to determine an appropriate coefficient α, multiply the first normal observation image data R by the coefficient α to obtain data αR, calculate the parameter W/(αR) using the data αR instead of the first normal observation image data R, and use the parameter W/(αR) instead of the parameter W/R. This coefficient α can be obtained in advance by performing preliminary experimentation using samples that have a known total hemoglobin amount tHb and degree of oxygen saturation Sat. In other words, before usage of the endoscope system 10 starts, it is preferable that the processor 200 performs preliminary experimentation using the aforementioned known samples to determine an appropriate coefficient α and store it.

The second parameter generation unit 535 generates a parameter (second parameter) N/W value for each pixel based on color image data stored in the internal memory 532. The parameter N/W value is the ratio of pixel values at the same pixel position in second special observation image data N, which is obtained by the image sensor 141 imaging biological tissue illuminated by light in the wavelength region R2 (N band), and the first special observation image data W, which is obtained by the image sensor 141 imaging biological tissue illuminated by light in the wavelength region R0 (W band). The wavelength region R2 (N band) is different from the wavelength region of white light WL, and is a wavelength region in which light absorption by biological tissue changes according to the degree of oxygen saturation Sat (second feature amount). As shown in the graphs (F1) and (F2) in FIG. 4, the parameter N/W is a parameter that has sensitivity to the degree of oxygen saturation Sat (second feature amount) of biological tissue, but does not have sensitivity to light scattering by biological tissue.

The second feature amount acquisition unit 536 acquires the degree of oxygen saturation Sat based on the parameter N/W value. The second feature amount acquisition unit 536 obtains the degree of oxygen saturation Sat for each pixel based on the parameter N/W value by retrieving and referencing the total hemoglobin amount tHb acquired by the first feature amount acquisition unit 534 and the numerical value table T2 (or function) that is held in the internal memory 532 and expresses the quantitative relationship between the parameter N/W and the degree of oxygen saturation Sat.

The feature amount distribution image generation unit 537 generates a feature amount distribution image that indicates the distribution of the total hemoglobin amount tHb (first feature amount) in biological tissue based on the total hemoglobin amount tHb obtained by the first feature amount acquisition unit 534. Alternatively, it generates a feature amount distribution image that indicates the distribution of the degree of oxygen saturation Sat (second feature amount) in biological tissue based on the degree of oxygen saturation Sat obtained by the second feature amount acquisition unit 536. Furthermore, the feature amount distribution image generation unit 537 generates a feature amount distribution image that indicates the distribution of the processing results of performing predetermined processing on the total hemoglobin amount tHb or the degree of oxygen saturation Sat.

The screen data of the feature amount distribution image created in this way is sent to the signal processing circuit 550.

The controller main body unit 538 manages and controls operations of constituent units of the processor 200 and the electronic endoscope 100.

The signal processing circuit 550 generates a video signal in a predetermined format (e.g., a format compliant with NTSC standards or DVI standards) based on screen data that was sent to the signal processing circuit 550 and stored in the video memory 540, and outputs the video signal. The video signal output from the signal processing circuit 550 is received by the monitor 300. As a result, an endoscopic image or the like captured by the electronic endoscope 100 is then displayed on the monitor 300.

Besides the above-described light source 430, the light source unit 400 also includes a condensing lens 440, a rotating filter 410, a filter control unit 420, and a condensing lens 450. Approximately parallel white light WL that exits the light source 430 is condensed by the condensing lens 440, passes through the rotating filter 410, is then again condensed by the condensing lens 450, and then enters the base end 131*b* of the light guide 131. Note that the rotating filter 410 can be moved between an application position on the optical path of the white light WL and a retracted position off the optical path by a moving means (not shown) such as a linear guideway.

Note that the configuration of the light source unit 400 is not limited to the configuration shown in FIG. 6. For example, a lamp that generates convergent light may be employed as the light source 430. In this case, a configuration may be employed in which, for example, white light WL is condensed before reaching the condensing lens 440, and then caused to enter the condensing lens 440 as diffused light.

Also, a configuration may be employed in which the condensing lens 440 is not used, and approximately parallel light generated by the light source 430 is caused to directly enter the rotating filter 410.

Also, in the case of using a lamp that generates convergent light, a configuration may be employed in which a collimator lens is used instead of the condensing lens 440 in order to cause white light WL that is in an approximately parallel state to enter the rotating filter 410. For example, in the case of using an interference type of optical filter such as a dielectric multilayer filter as the rotating filter 410, by causing approximately parallel white light WL to enter the rotating filter 410, the angle of incidence of the white light WL on the optical filter can be made uniform, thus making it possible to obtain more favorable filter characteristics.

Also, a lamp that generates diverging light may be applied as the light source 430. In this case as well, a configuration can be employed in which a collimator lens is used instead of the condensing lens 440 in order to cause approximately parallel white light WL to enter the rotating filter 410.

The rotating filter 410 is a disc-type optical unit that includes multiple optical filters, and is configured such that the pass wavelength region is switched according to the rotation angle. The rotation angle of the rotating filter 410 is controlled by the filter control unit 420, which is connected to the controller 530. The controller 530 controls the rotation angle of the rotating filter 410 via the filter control unit 420, thus switching the spectrum of illumination light IL that passes through the rotating filter 410 and is supplied to the light guide 131.

Figure 9:
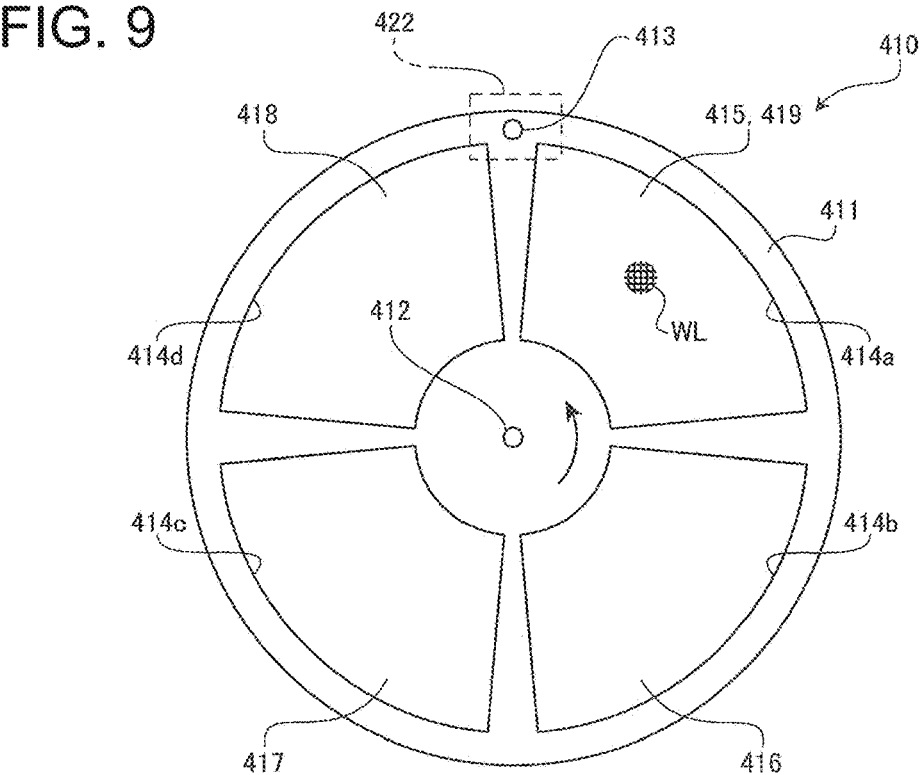
FIG. 9 is an external view of one example of a rotating filter used in the embodiment.

FIG. 9 is an external view (front view) of the rotating filter 410. The rotating filter 410 includes an approximately disc-shaped frame 411 and four fan-shaped optical filters 415, 416, 417, and 418. Three fan-shaped windows 414*a*, 414*b*, and 414*c* are formed with equal gaps therebetween around the central axis of the frame 411, and the optical filters 415, 416, 417, and 418 are respectively fitted into the windows 414*a*, 414*b*, 414*c*, and 414*d*. Note that the optical filters of the present embodiment are all dielectric multilayer filters, but another type of optical filter (e.g., an absorption optical filter or an etalon filter that uses a dielectric multilayer film as a reflection film) may be used. Note that the optical filter of the optical filter 417 has the same filter characteristics as the optical filter of the optical filter 418, and therefore a description will not be given below for the optical filter 415. Note that the rotating filter 410 shown in FIG. 9 is constituted by four optical filters, but may be constituted by three optical filters 415, 416, and 418.

Also, a boss hole 412 is formed on the central axis of the frame 411. An output shaft of a servo motor (not shown) of the filter control unit 420 is inserted in and fixed to the boss hole 412, and the rotating filter 410 rotates along with the output shaft of the servo motor.

Although the state where white light WL enters the optical filter 415 is shown in FIG. 9, when the rotating filter 410 rotates in the direction indicated by the arrow, the optical filter that the white light WL enters successively switches between the optical filters 415, 416, and 418 in this order, and thus the spectrum of illumination light IL that passes through the rotating filter 410 switches successively.

The optical filters 415 and 416 are optical bandpass filters that selectively allow light in the 550 nm band to pass. As shown in FIG. 1, the optical filter 415 is configured to allow light in the wavelength region from the isosbestic points E1 to E4 (i.e., the wavelength region R0 (W band)) to pass with low loss, and block light in other wavelength regions. Also, the optical filter 416 is configured to allow light in the wavelength region from the isosbestic points E2 to E3 (i.e., the wavelength region R2 (N band)) to pass with low loss, and block light in other wavelength regions.

As shown in FIG. 1, the wavelength region R1 includes the peak wavelength of the absorption peak P1 derived from oxygenated hemoglobin, the wavelength region R2 includes the peak wavelength of the absorption peak P2 derived from reduced hemoglobin, and the wavelength region R3 includes the peak wavelength of the absorption peak P3 derived from oxygenated hemoglobin. Also, the wavelength region R0 includes the peak wavelengths of the three absorption peaks P1, P2, and P3.

Also, the W band and the N band, which are the pass wavelength regions of the optical filters 415 and 416 (FIG. 1), are included in the pass wavelength region of the G color filter of the color filter 141a (FIG. 8). Accordingly, image data of a subject image formed by light that passes through the optical filters 415 and 416 is captured by the light receiving elements on which the G color filters are mounted in the image sensor 141, is obtained as G digital image data, and is data for the same wavelength region as the G wavelength region in the RGB color space. Accordingly, the above-described first special observation image data W and the second special observation image data N are data for the same wavelength region as the G wavelength region in the RGB color space.

Here, light that passes through the optical filter 415 is first special light that illuminates the biological tissue in order to obtain first special observation image data, and light that passes through the optical filter 416 is second special light that illuminates the biological tissue in order to obtain second special observation image data. The first special observation image data is used in order to acquire "W" in the above-described parameter "W/R", and the parameter "W/R" is used in order to obtain the total hemoglobin amount tHb. The second special observation image data is used in order to acquire "N" in the above-described parameter "N/W", and the parameter "N/W" is used in order to obtain the degree of oxygen saturation Sat.

Regarding the absorption of the first special light by the biological tissue, the wavelength region of the first special light, that is to say the R0 wavelength region, is set so as to be dependent on the total hemoglobin amount tHB (first feature amount), but not dependent on the degree of oxygen saturation Sat (second feature amount). Also, regarding the absorption of the second special light by the biological tissue, the wavelength region of the second special light, that is to say the wavelength region R2, is set so as to be dependent on both the total hemoglobin amount tHb (first feature amount) and the degree of oxygen saturation Sat (second feature amount).

Also, the optical filter 418 is an ultraviolet cut filter, and illumination light IL that passes through the optical filter 418 (i.e., white light) is used in the capture of a normal observation image. Accordingly, white light that passes through the optical filter 418 is the white light WL emitted by the light source 430 and has little variation in the visible wavelength region, and therefore is called white light WL. This white light WL is used in order to acquire "R" in the above-described parameter "W/R", and the parameter "W/R" is used in order to obtain the total hemoglobin amount tHb.

Note that a configuration is possible in which the optical filter 418 is not used, and the window 414c of the frame 411 is open. Also, in the present specification, illumination light IL that passes through the optical filters 415 and 416 is also called special light (first special observation light, second special observation light), and white light (or wide band light) that passes through the optical filter 418 is also called normal light (normal observation light).

Also, a light attenuation filter (ND filter) 419 is attached over the optical filter 415 in the window 414a. The light attenuation filter 419 has no wavelength dependency over the entire visible light range, and merely reduces the quantity of light with no change in the spectrum of illumination light IL. By using the light attenuation filter 419, the quantity of illumination light IL that passes through the optical filter 415 and the light attenuation filter 419 is adjusted to approximately the same as the quantity of illumination light IL that passes through the optical filter 416. Accordingly, regardless of whether illumination light IL that passed through the optical filter 415 or the optical filter 416 is used, it is possible to capture an image with the same exposure time and appropriate exposure.

In the present embodiment, a fine metal mesh is used as the light attenuation filter 419. Besides a metal mesh, another type of light attenuation filter such as a slit or half mirror type may be used. Also, a configuration is possible in which a light attenuation filter is not used, and the transmissivities of the optical filters 415 and 416 themselves are adjusted. Also, a light attenuation filter may be attached to the windows 414b and 414c as well. Moreover, the passing light quantity may be adjusted by changing the central angles (i.e., opening areas) of the windows 414a to 414c. Furthermore, a configuration is possible in which a light attenuation filter is not used, and the exposure time is adjusted for each optical filter that is used.

A through-hole 413 is formed in the peripheral edge portion of the frame 411. The through-hole 413 is formed at the same position (phase) as the boundary portion between the window 414a and the window 414c in the rotation direction of the frame 411. A photo interrupter 422 for detecting the through-hole 413 is arranged in the periphery of the frame 411 so as to surround a portion of the peripheral edge portion of the frame 411. The photo interrupter 422 is connected to the filter control unit 420.

In this way, the optical apparatus 400 switches between emitting white light and special light with use of the rotating optical filter.

Note that the light source apparatus 400 of the present embodiment is configured such that light with different wavelength regions is emitted by causing light emitted from one light source 430 to pass through an optical filter, but instead of the light source lamp 430, a semiconductor light source, such as LEDs or laser devices that output laser light, that emits different types of light with different wavelength regions can be used in place of the light source 400. In this case, the rotating filter 410 does not need to be used.

The endoscope apparatus 1 of the present embodiment has two operating modes, namely a normal observation mode and a spectral analysis mode. The normal observation mode is an operating mode for capturing color images using white light WL. The spectral analysis mode is a mode for performing spectral analysis based on digital image data obtained using the first special light and the second special light, which are illumination light IL that passes through the optical filters 415 and 416 respectively, and displaying a biomolecule distribution image of biological tissue (e.g., a degree of oxygen saturation distribution image). The operating mode of the endoscope apparatus 1 is switched by a user operation performed on an operation panel (not shown) of the processor 200 or an operation button (not shown) of the electronic endoscope 100, for example.

In the normal observation mode, the controller 530 controls the moving means to move the rotating filter 410 from the application position to the retracted position. Note that in the spectroscopic analysis mode, the rotating filter 410 is arranged at the application position. Also, in the case where the rotating filter 410 does not have a moving means, the controller 530 controls the filter control unit 420 to stop the rotating filter 410 at a position at which white light WL enters the optical filter 418. Then, digital image data obtained by the image sensor 141 is subjected to predetermined image processing such as demosaicing, and then converted into a video signal and displayed on the screen of the monitor 300.

In the spectral analysis mode, the controller 530 controls the filter control unit 420 to drive the rotating filter 410 to rotate at a constant rotational frequency and successively capture images of the biological tissue T using illumination light IL that passes through the optical filters 415, 416, and 418. A feature amount distribution image is created using image data of a special observation image acquired using illumination light IL that passes through the optical filters 415 and 416 and image data of a normal observation image acquired using illumination light IL that passes through the optical filter 418, and the controller 530 generates screen data that arranges the feature amount distribution image and the normal observation image side-by-side. This screen data is then converted into a video signal and displayed on the monitor 300.

In the spectroscopic analysis mode, the filter control unit 420 detects the phase of rotation of the rotating filter 410 based on the timing of detection of the through-hole 413 by the photo interrupter 422, compares the detected phase with the phase of a timing signal supplied by the controller 530, and adjusts the phase of rotation of the rotating filter 410. The timing signal from the controller 530 is synchronized with the drive signal for the image sensor 141. Accordingly, the rotating filter 410 is driven to rotate at a substantially constant rotational frequency in synchronization with the driving of the image sensor 141. Specifically, the rotation of the rotating filter 410 is controlled such that the one of the optical filters 415, 416, and 418 (windows 414a-c) that white light WL enters is switched each time one image (three R, G, and B frames) is captured by the image sensor 141.

In this way, the processor 200 includes both functionality as a video processor that processes imaging signals output from the image sensor 141 of the electronic endoscope 100, and functionality as a light source apparatus that supplies illumination light IL, which is for illuminating biological tissue T that is the imaging subject, to the light guide 131 of the electronic endoscope 100.

Figure 10:
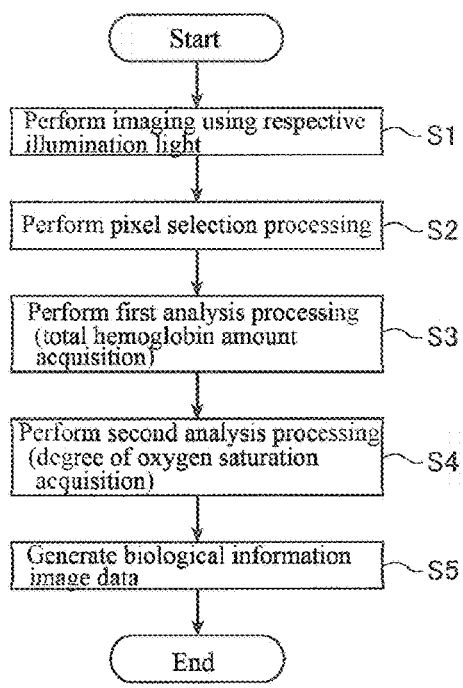
FIG. 10 is a flowchart illustrating an example of spectral analysis processing according to the embodiment.

Next, spectral analysis processing executed in the spectral analysis mode will be described. FIG. 10 is a flowchart showing a procedure of spectral analysis processing.

If the spectral analysis mode has been selected by a user operation, the filter control unit 420 drives the rotating filter 410 to rotate at a constant rotational frequency as described above. Illumination light IL is successively supplied from the light source unit 400, and then through the optical filters 415, 416, and 418, and images are successively captured using the respective types of illumination light IL (S1). Specifically, G digital image data W(x,y) obtained using illumination light IL that passes through the optical filter 415 (first special light in the wavelength region R0 (W band)), G digital image data N(x,y) obtained using illumination light IL that passes through the optical filter 416 (second special light in the wavelength region R2 (N band)), and R digital image data R(x,y), G digital image data G (x,y), and B digital image data B (x,y) obtained using illumination light IL that passes through the optical filter (ultraviolet cut filter) 418 (normal light, white light WL) are stored in the internal memory 532 of the controller 530.

Next, the image processing unit 500 performs pixel selection processing S2 for selecting pixels that are to be subjected to subsequent analysis processing (processing S3-S8), using the R digital image data R (x,y), the G digital image data G (x,y), and the B digital image data B (x,y) acquired in processing S1. This pixel selection processing S2 is performed by the controller 530.

At locations where blood is not included, or locations where the biological tissue color is dominantly influenced by a substance other than hemoglobin, even if the degree of oxygen saturation Sat or blood flow is calculated based on color information of the pixel, a meaningful value is not obtained, but rather is simply noise. If such noise is presented to a physician, it will not only be a hindrance to the physician's diagnosis, but also have the harmful effect of placing an unnecessary burden on the image processing unit 500 and reducing the processing speed. In view of this, the analysis processing of the present embodiment is configured such that pixels suited to analysis processing (i.e., pixels recording the spectroscopic features of hemoglobin) are selected, and analysis processing is performed on only the selected pixels.

In pixel selection processing S2, only pixels that satisfy all of the conditions of Expressions 4, 5, and 6 below are selected as target pixels for analysis processing.

$$B(x,y)/G(x,y) > \alpha_1 \qquad \text{Expression 4}$$

$$R(x,y)/G(x,y) > \alpha_2 \qquad \text{Expression 5}$$

$$R(x,y)/B(x,y) > \alpha_3 \qquad \text{Expression 6}$$

Here, a1, a2, and a3 are positive constants.

The above three conditional expressions are set based on the magnitude relationship of G component value<B component value<R component value in the transmission spectrum of blood. Note that pixel selection processing S2 may be performed using only one or two of the above three conditional expressions (e.g., using only Expressions 5 and 6 when focusing on the color red which is specific to blood).

Next, the controller 530 of the image processing unit 500 performs first analysis processing S3. The internal memory 532 of the controller 530 holds the numerical value table T1 (or function) that expresses the quantitative relationship between the total hemoglobin amount tHb and the parameter W/R shown in the graphs (D1) and (D2) in FIG. 4. In the first analysis processing S3, this numerical value table T1 is used to acquire the value of the total hemoglobin amount tHb based on the G digital image data W(x,y) and the R digital image data R(x,y) acquired in processing S1.

Specifically, first, the parameter W/R(x,y) for each pixel (x,y) is calculated using Expression 7

$$W/R(x,y) = W(x,y)/R(x,y) \qquad \text{Expression 7}$$

Next, the numerical value table T1 is referenced to read out and acquire the value of the total hemoglobin amount tHb(x,y) that corresponds to the value of the parameter W/R(x,y) calculated using Expression 7.

The quantitative relationship in the numerical value table T1 (and the later-described numerical value table T2) held in the internal memory 532 is obtained in advance by theoretical calculation or experimentation. Note that although a complete one-to-one correspondence does not exist for the value of the total hemoglobin amount tHb and the value of the parameter W/R in (D1) and (D2) in FIG. 4, a representative one-to-one quantitative relationship (e.g., average value or mean value) is held in the numerical value table T1 for the total hemoglobin amount tHb and the parameter W/R. For this reason, the total hemoglobin amount tHb can be uniquely determined based on the value of the parameter W/R using the numerical value table T1.

Next, the controller 530 of the image processing unit 500 performs second analysis processing S4. The internal memory 532 of the controller 530 holds the numerical value table T2 (or function) that expresses the quantitative relationship between the total hemoglobin amount tHb, the parameter N/W, and the degree of oxygen saturation Sat shown in the graph (F2) in FIG. 4. Three numerical values (called a "numerical value set"), namely the total hemoglobin amount tHb, the parameter N/W, and the degree of oxygen saturation Sat, are held in association with each other in the numerical value table T2. In the second analysis processing S4, this numerical value table T2 is used to acquire the value of the degree of oxygen saturation Sat(x,y) for each pixel based on the G digital image data W(x,y) and N(x,y) acquired in processing S1 and the value of the total hemoglobin amount tHb(x,y) acquired in first analysis processing S3.

Specifically, first, the parameter N/W(x,y) for each pixel (x,y) is calculated using Expression 8.

$$N/W(x,y)=N(x,y)/W(x,y) \quad \text{Expression 8}$$

Next, for each pixel (x,y), the numerical value table T2 is referenced to extract the numerical value set that is closest to the value of the total hemoglobin amount tHb(x,y) acquired in first analysis processing S3 and the value of the parameter N/W(x,y) calculated using Expression 8, and then the value of the degree of oxygen saturation Sat in the extracted numerical value set is read out and acquired as the value of the degree of oxygen saturation Sat(x,y) at that pixel (x,y).

The internal memory 532 of the controller 530 stores a numerical value table (or function) that expresses the relationship between the degree of oxygen saturation Sat(x,y) and display colors (pixel values). Then, in processing S5 (FIG. 6), the controller 530 references this numerical value table (or function), and generates biological information image data using pixel values that indicate the display colors corresponding to the degree of oxygen saturation Sat(x,y) obtained in processing S4.

The controller 530 then generates normal observation image data based on the R digital image data R(x,y), the G digital image data G(x,y), and the B digital image data B(x,y) that were obtained using illumination light IL (white light) that passes through the optical filter (ultraviolet cut filter) 418.

Figure 11A:
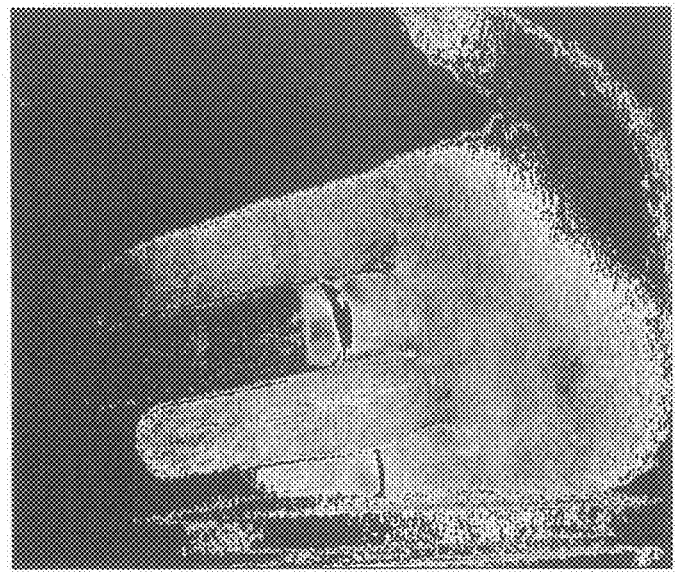
FIGS. 11A and 11B show examples of display of image information generated by the endoscope system according to the embodiment of the present invention, where
Figure 11B:
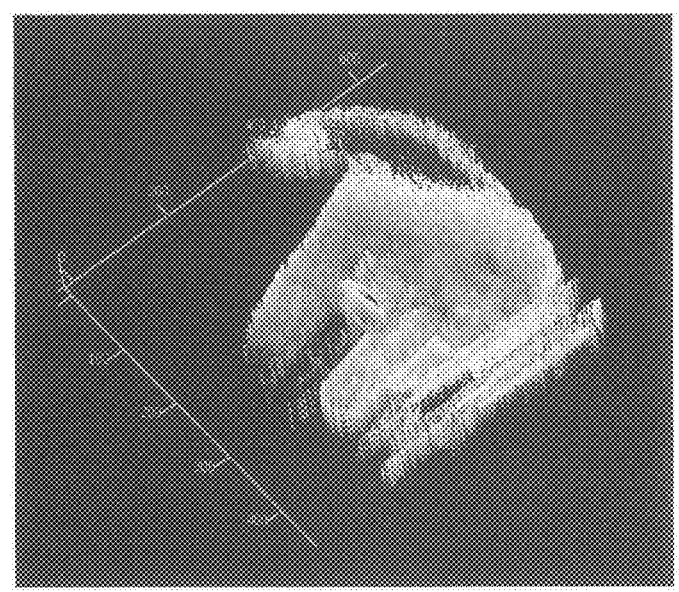

FIG. 11A and FIG. 11B show examples of the display of image data generated by the controller 530. FIG. 11A illustrates an example of the display of degree of oxygen saturation distribution image data (two-dimensional display) generated based on the degree of oxygen saturation Sat(x,y) acquired by processing S5 described above. Also, FIG. 11B illustrates an example of the display of degree of oxygen saturation distribution image data (three-dimensional display) generated in a three-dimensional graph format in which the degree of oxygen saturation is the vertical axis. Note that FIGS. 11A and 11B show the observation of a right hand in the state where an elastic band constricts the vicinity of the proximal interphalangeal joint of the middle finger. On the distal side of the constricted site of the right middle finger, the flow of blood is inhibited by the constriction, and therefore it is seen that the degree of oxygen saturation Sat is low.

The controller 530 then uses the generated degree of oxygen saturation distribution image data and normal observation image data to generate screen data in which the normal observation image and the degree of oxygen saturation distribution image are displayed side-by-side in one screen, and stores the screen data in the video memory 540. Note that in accordance with a user operation, the feature amount distribution image generation unit 537 of the controller 530 can generate various types of display screens, such as a display screen that displays only the degree of oxygen saturation distribution image, a display screen that displays only the normal observation image, a display screen that displays supplementary information such as patient ID information and observation conditions in a superimposed manner on the degree of oxygen saturation distribution image and/or the normal observation image, or a display screen that displays a new feature amount distribution image created with a combination of the total hemoglobin amount tHb and the degree of oxygen saturation Sat.

Malignant tumor tissue has a higher total hemoglobin amount tHb than normal tissue due to angiogenesis, and also exhibits remarkable oxygen metabolism, and therefore it is known that the degree of oxygen saturation Sat is lower than that of normal tissue. In view of this, the feature amount distribution image generation unit 537 of the controller 530 can perform processing to extract the pixels for which the total hemoglobin amount tHb acquired by first analysis processing S3 is greater than a predetermined reference value (first reference value), and for which the degree of oxygen saturation Sat acquired by second analysis processing S4 is less than a predetermined reference value (second reference value), perform enhanced display processing on corresponding pixels of normal observation image data for example to generate enhanced lesion site image data, and display the enhanced lesion site image on the monitor 300 along with the normal observation image and/or the degree of oxygen saturation distribution image (or on its own).

Examples of enhanced display processing include processing for increasing the pixel values of corresponding pixels, processing for changing the hue (e.g., processing for increasing the redness by increasing the R component, or processing for rotating the hue by a predetermined angle), and processing for flashing corresponding pixels (or periodically changing the hue).

Also, a configuration is possible in which, instead of generating enhanced lesion site image data, the controller 530 calculates an indicator Z(x,y) that indicates the degree of suspicion of a malignant tumor based on the deviation of the degree of oxygen saturation Sat(x,y) from an average value and the deviation of the total hemoglobin amount tHb(x,y) from an average value, and generate image data in which the pixel values are the indicator Z (malignancy suspicion image data).

The endoscope apparatus 1 of the present embodiment is configured to generate the parameter "W/R" (first parameter) that has sensitivity to the total hemoglobin amount tHb (first feature amount) of biological tissue, but does not have sensitivity to light scattering by biological tissue based on color image data obtained by the image sensor 141, and therefore error arising from light scattering in the total hemoglobin amount tHb (first feature amount) is reduced, and more precise spectroscopic analysis can be performed.

Also, in the endoscope apparatus 1, the ratio W/R (first parameter) is generated based on image data "W" that has a component in wavelength region that has sensitivity to the total hemoglobin amount tHb (first feature amount) of biological tissue and has sensitivity to light scattering by biological tissue, and image data "R" that has a component in a wavelength region that does not have sensitivity to the total hemoglobin amount tHb (first feature amount) of biological tissue, but has sensitivity to light scattering by the biological tissue, thus making it possible to generate the ratio W/R (first parameter) easily and with quick processing. In particular, from the viewpoint of the operator carrying out a procedure while operating the electronic endoscope 100 in order to find a position of interest in a feature amount distribution image of biological tissue so as to specify and observe a lesion site of biological tissue, it is preferable that the feature amount distribution images are displayed in real-time. From this viewpoint, it is preferable that the ratio W/R (first parameter) is generated easily and quickly based on the two pieces of image data described above.

The aforementioned two pieces of image data are the first special observation image data W, which was obtained by imaging biological tissue illuminated by the first special light in the wavelength region R0 (W band) which is different from the wavelength region of white light WL, and in which light absorption by biological tissue changes according to the total hemoglobin amount tHb (first feature amount), and the first normal observation image data R, which is the R component of normal observation image data in the RGB color space obtained by imaging biological tissue illuminated by white light WL, and in particular, the first special observation image data W is obtained using illumination by the first special light, and therefore the obtained ratio W/R is sensitive to change in absorption in the wavelength region R0 (W band). For this reason, it is possible to calculate a precise total hemoglobin amount tHb (first feature amount) based on the ratio W/R.

The first normal observation image data R used in calculation of the ratio W/R (first parameter) is data of an image captured via the R color filter of the image sensor 141, and therefore it is possible to acquire the ratio W/R, quickly and without the need to separate light into different wavelengths and retrieve the component for a predetermined wavelength region, thus making it possible to display the feature amount distribution image in real-time in the electronic endoscope 100.

Also, the light source apparatus 400 is configured to use an optical filter to obtain the first special light, which is used in the spectral analysis mode for displaying a feature amount distribution image of biological tissue, from white light generated by a white light source used in the normal observation mode for displaying images of biological tissue, thus making it possible to simplify the apparatus configuration, realize a reduction in the size of the processor 200, and ensure space in the medical setting where a procedure is carried out while operating the electronic endoscope 100.

The controller 530 stores data expressing the quantitative relationship between the ratio W/R (first parameter) and the total hemoglobin amount tHb (first feature amount), and the first feature amount acquisition unit 534 obtains the total hemoglobin amount tHb of biological tissue using the data expressing the quantitative relationship, and therefore the present embodiment makes it possible to calculate the total hemoglobin amount tHb and the degree of oxygen saturation Sat more efficiently than in the case where the total hemoglobin amount tHb and the degree of oxygen saturation Sat are calculated without using data expressing the quantitative relationship each time color image data is acquired. For this reason, the calculation circuitry of the processor 200 can be made smaller, thus making it possible to provide a processor 200 that is low-cost, generates less heat, and consumes less power even when generating high-quality images.

The first special observation image data W used in obtaining the ratio W/R (first parameter) is data of the same wavelength region as the G wavelength region in the RGB color space, and furthermore is data of an image captured by the image sensor 141 via the G color therefore it is possible to acquire the ratio W/R quickly and without the need to separate light into different wavelengths and retrieve the component for a predetermined wavelength region, thus making it possible to display the feature amount distribution image in real-time in the electronic endoscope 100.

Furthermore, the second parameter generation unit 535 of the processor 200 is configured to generate the ratio N/W (second parameter) that has sensitivity to the degree of oxygen saturation Sat (second feature amount) of biological tissue, but does not have sensitivity to light scattering, based on color image data, and the second feature amount acquisition unit 537 is configured to acquire the degree of oxygen saturation Sat (second feature amount) based on the total hemoglobin amount tHb (first feature amount) and the ratio N/W (second parameter), thereby reducing error arising from light scattering in the degree of oxygen saturation Sat (second feature amount) and making it possible to perform more precise spectroscopic analysis.

The light source apparatus 400 is configured to emit second special light that has a different wavelength region than white light and is absorbed by biological tissue differently according to the degree of oxygen saturation Sat (second feature amount), and the ratio N/W is obtained using illumination by the second special light, and therefore the obtained ratio N/W is sensitive to change in absorption in the wavelength region R2 (N band). For this reason, it is possible to calculate a precise degree of oxygen saturation Sat (second feature amount) based on the ratio N/W.

In the present embodiment, the wavelength region of the first special light used to obtain the ratio N/W is set such that the light absorption of the first special light by biological tissue is dependent on the total hemoglobin amount tHb (first feature amount), but not dependent on the degree of oxygen saturation Sat (second feature amount), or more specifically set to the wavelength region R0 (W band) as shown in FIG. 1, and therefore it is possible to calculate a precise degree of oxygen saturation Sat (second feature amount) based on the ratio N/W.

In the present embodiment, the wavelength region of the second special light used to calculate the ratio N/W is set such that the light absorption of the second special light by biological tissue is dependent on both the total hemoglobin amount tHb (first feature amount) and the degree of oxygen saturation Sat (second feature amount), and therefore it is possible to calculate a precise degree of oxygen saturation Sat (second feature amount) based on the ratio N/W and the total hemoglobin amount tHb obtained based on the ratio W/R.

The second special observation image data N used in obtaining the ratio N/W (second parameter) is data of the same wavelength region as the G wavelength region in the RGB color space, and furthermore is data of an image captured by the image sensor 141 via the G color filter, and therefore it is possible to acquire the ratio N/W quickly and without the need to separate light into different wavelengths and retrieve the component for a predetermined wavelength region, thus making it possible to display the feature amount distribution image in real-time in the electronic endoscope 100.

The feature amount distribution image generation unit 537 of the controller 530 generates a feature amount distribution image that shows a distribution of the total hemoglobin amount tHb (first feature amount) of biological tissue or the degree of oxygen saturation Sat (second feature amount based) on the total hemoglobin amount tHb (first feature amount) or the degree of oxygen saturation Sat (second feature amount), or a feature amount distribution image that shows the results of processing performed based on the total hemoglobin amount tHb (first feature amount) and the degree of oxygen saturation Sat (second feature amount), and therefore the endoscope apparatus 1 can provide assistive images that are useful for identifying a lesion site of biological tissue to the operator carrying out a procedure while operating the electronic endoscope 100.

Although an embodiment of the present invention has been described above, the present invention is not limited to the above configuration, and various modifications can be made within the scope of the technical idea of the present invention.

Also, the present embodiment employs a configuration in which in the first analysis processing S1, the parameter W/R is calculated based on special observation and normal observation image data, and the total hemoglobin amount tHb is determined based on the relationship between the parameter W/R and the total hemoglobin amount tHb expressed in the graphs (D1) and (D2) in FIG. 4, but the present invention is not limited to this configuration. For example, it is possible to employ a configuration in which in the first analysis processing S1, the parameter W/(R+G) is calculated based on special observation and normal observation image data, and the total hemoglobin amount tHb is determined based on the relationship between the total hemoglobin amount tHb and the parameter W/(R+G) expressed in the graphs (G1) and (G2) in FIG. 5. In this case, scattering has very little influence on the parameter W/(R+G), and therefore it is possible to perform measurement with even less noise attributed to scattering.

Note that the wavelength region of the image including the R component and the G component varies depending on the type of image sensor 141 and the filter characteristics of the color filter 141a, and the wavelength region of the image including the R component and the G component also varies depending on error between apparatuses in the endoscope system 10 as well. For this reason, it is preferable to determine appropriate coefficients β and γ in advance, use the coefficients β and γ to obtain the sum βR+γG by performing weighted addition on the first normal observation image data R and the second normal observation image data G that are the R component and the G component of normal observation image data, obtain the parameter W/(βR+γG) by performing calculation using the sum βR+γG instead of the sum (R+G), and then use the parameter W/(βR+γG) instead of the parameter W/(R+G). These coefficients β and γ can be obtained in advance by performing preliminary experimentation using samples that have a known total hemoglobin amount tHb and degree of oxygen saturation. In other words, before usage of the endoscope system 10 starts, it is preferable that the processor 200 performs preliminary experimentation using the aforementioned known samples to determine appropriate coefficients β and γ and store them.

Also, in the present embodiment, in the second analysis processing S2, the parameter N/W is calculated based on special observation image data, and the degree of oxygen saturation Sat is determined based on the relationship between the parameter N/W, the total hemoglobin amount tHb, and the degree of oxygen saturation Sat expressed by the graph (F2) in FIG. 4, but the present invention is not limited to this configuration. For example, a configuration can be employed in which in the second analysis processing S2, the parameter B/G is calculated based on normal observation image data, and the degree of oxygen saturation Sat is determined based on the relationship between the parameter B/G, the total hemoglobin amount tHb, and the degree of oxygen saturation Sat expressed by the graph (C2) in FIG. 4. In this case, there is no need to perform special observation using the optical filter 416 in order to acquire the parameter N, thus making it possible to eliminate the optical filter 426 and acquire biological information such as the degree of oxygen saturation Sat with a lower processing amount and in a shorter time.

Also, in the present embodiment, the present invention is applied to the analysis of the concentration distribution of hemoglobin in biological tissue, but the present invention can also be applied to the analysis of the concentration distribution of another biological substance (e.g., a secretion such as a hormone) that changes the color of biological tissue.

Also, the image sensor 141 the present embodiment is described as an image sensor for color image capturing that includes R, G, and B primary-color color filters on the front side, but there is no limitation to this configuration, and an image sensor for color image capturing that includes Y, Cy, Mg, and G complementary-color color filters for example may be used.

Also, the image sensor 141 of the present embodiment is described as an image sensor for color image capturing that includes an on-chip color filter 141a, but there is no limitation to this configuration, and a configuration is possible in which, for example, an image sensor for black-and-white image capturing is used and includes a so-called frame sequential color filter. Also, the color filter 141a is not limited to having an on-chip configuration, and can be arranged in the optical path between the light source 430 and the image sensor 141.

Also, although the rotating filter 410 is used in the present embodiment, the present invention is not limited to this configuration, and another type of variable wavelength filter that enables switching the pass wavelength region can be used.

Also, in the present embodiment, a configuration is applied in which the rotating filter 410 is provided on the light source side and performs filtering on white light WL, but the present invention is not limited to this configuration, and a configuration is possible in which the rotating filter 410 is provided on the image sensor side (e.g., between the objective optical system 121 and the image sensor 131) and performs filtering on returning light from the subject.

Also, in the present embodiment, a configuration is applied in which in the spectroscopic analysis mode, images are captured at a predetermined time interval while rotating the rotating filter 410 at a constant rotational frequency, but the present invention is not limited to this configuration, and a configuration is possible in which, for example, the rotation position of the rotating filter 410 is changed in a stepwise manner at a predetermined time interval and Images are captured while the rotating filter 410 is in the stopped state.

Also, in the present embodiment, a white light source such as a xenon lamp is used as the light source that generates wide band light for illumination, but it is possible to use a light source that generates non-white wide band light having a sufficient light quantity over the entire pass wavelength region of the optical filters that are used.

Also, although transmissive optical filters are used in the present embodiment, reflective optical filters that reflect a pass wavelength region may be used.

Also, although the present embodiment is an endoscope system (endoscope apparatus), the present invention is also applicable to an analyzing apparatus that uses a digital camera (e.g., a digital single lens reflex camera or a digital video camera). For example, if the imaging unit is applied to a digital still camera, it is possible to observe body surface tissue or observe brain tissue during craniotomy (e.g., perform a rapid brain blood flow test).

In this case, the analyzing apparatus includes: a light source apparatus; an imaging unit that includes an image sensor configured to generate color image data by imaging biological tissue illuminated by light emitted by the light source apparatus; and a processor that has a first parameter generation unit configured to generate a first parameter that has sensitivity to a first feature amount of the biological tissue but does not have sensitivity to light scattering by the biological tissue based on the color image data obtained by the imaging performed by the image sensor, and a first feature amount acquisition unit configured to acquire the first feature amount based on the first parameter.

DESCRIPTION OF REFERENCE SIGNS

1 Endoscope apparatus
100 Electronic endoscope
110 Insertion tube
111 Insertion tube distal end portion
121 Objective optical system
122 Imaging unit
131 Light guide
131a Distal end portion
131b Base end portion
132 Lens
141 Image sensor
141a Color filter
142 Cable
200 Processor
300 Monitor
400 Light source unit
410 Rotating filter
420 Filter control unit
430 Light source
440 Condensing lens
450 Condensing lens
500 Image processing unit
510 A/D conversion circuit
520 Temporary storage memory
530 Controller
532 Internal memory
533 First parameter generation unit
534 First feature amount acquisition unit
535 Second parameter generation unit
536 Second feature amount acquisition unit
537 Feature amount distribution image generation unit
538 Controller main body unit
540 Video memory
550 Signal processing circuit

The invention claimed is:

1. An endoscope system comprising:
a light source apparatus configured to emit first special light that has a different wavelength region from white light and is absorbed by biological tissue differently according to a first feature amount of the biological tissue;
an endoscope having an imaging unit that comprises an image sensor configured to generate color image data by imaging the biological tissue illuminated by light emitted by the light source apparatus; and
a processor that has a first parameter generation unit and a first feature amount acquisition unit,
the first parameter generation unit configured to generate, based on the color image data, a first parameter that is a ratio W/R of a first special observation image data W and a first normal observation image data R,
the first special observation image data W being obtained by imaging the biological tissue illuminated by the first special light, and being color image data X of an image that has a component in a wavelength region that has sensitivity to the first feature amount of the biological tissue and has sensitivity to light scattering by the biological tissue; and
the first normal observation image data R being an R component of normal observation image data in an RGB color space obtained by imaging the biological tissue illuminated by the white light, and being color image data Y of an image that has a component in a wavelength region that does not have sensitivity to the first feature amount of the biological tissue but has sensitivity to light scattering by the biological tissue,
the first feature amount acquisition unit configured to acquire the first feature amount based on the first parameter.

2. An endoscope system comprising:
a light source apparatus configured to emit first special light that has a different wavelength region from white light and is absorbed by biological tissue differently according to a first feature amount of the biological tissue;
an endoscope having an imaging unit that comprises an image sensor configured to generate color image data by imaging the biological tissue illuminated by light emitted by the light source apparatus; and
a processor that has a first parameter generation unit and a first feature amount acquisition unit,
the first parameter generation unit configured to generate, based on the color image data, a first parameter that is a ratio $W/(\alpha R)$ of a first special observation image data W and a data $\alpha R$,
the first special observation image data W being obtained by imaging the biological tissue illuminated by the first special light, and being color image data X of an image that has a component in a wavelength region that has sensitivity to the first feature amount of the biological tissue and has sensitivity to light scattering by the biological tissue; and
the data $\alpha R$ being obtained by multiplying a first normal observation image data R by a coefficient set in advance, the first normal observation image data R being an R component of normal observation image data in an RGB color space obtained by imaging the biological tissue illuminated by the white light, and being color image data Y of an image that has a component in a wavelength region that does not have sensitivity to the first feature amount of the biological tissue but has sensitivity to light scattering by the biological tissue,
the first feature amount acquisition unit configured to acquire the first feature amount based on the first parameter.

3. An endoscope system comprising:
a light source apparatus configured to emit first special light that has a different wavelength region from white light and is absorbed by biological tissue differently according to a first feature amount of the biological tissue;
an endoscope having an imaging unit that comprises an image sensor configured to generate color image data by imaging the biological tissue illuminated by light emitted by the light source apparatus; and a processor that has a first parameter generation unit and a first feature amount acquisition unit, the first parameter generation unit configured to generate, based on the color image data, a first parameter that is a ratio W/(R+G) of a first special observation image data W and a sum R+G, the first special observation image data W being obtained by imaging the biological tissue illuminated by the first special light, and being color image data X of an image that has a component in a wavelength region that has sensitivity to the first feature amount of the biological tissue and has sensitivity to light scattering by the biological tissue; and the sum R+G being a sum of first normal observation image data R and second normal observation image data G that are respectively an R component and a G component of normal observation image data in an RGB color space obtained by imaging the biological tissue illuminated by the white light, and being color image data Y of an image that has a component in a wavelength region that does not have sensitivity to the first feature amount of the biological tissue but has sensitivity to light scattering by the biological tissue, the first feature amount acquisition unit configured to acquire the first feature amount based on the first parameter.

4. An endoscope system comprising:

a light source apparatus configured to emit first special light that has a different wavelength region from white light and is absorbed by biological tissue differently according to a first feature amount of the biological tissue;

an endoscope having an imaging unit that comprises an image sensor configured to generate color image data by imaging the biological tissue illuminated by light emitted by the light source apparatus; and a processor that has a first parameter generation unit and a first feature amount acquisition unit, the first parameter generation unit configured to generate, based on the color image data, a first parameter that is a ratio W/(βR+γG) of a first special observation image data W and a sum βR+γG, the first special observation image data W being obtained by imaging the biological tissue illuminated by the first special light, and being color image data X of an image that has a component in a wavelength region that has sensitivity to the first feature amount of the biological tissue and has sensitivity to light scattering by the biological tissue; and the sum βR+γG being a sum of obtained by using a coefficient β and a coefficient γ that are set in advance to perform weighted addition on first normal observation image data R and second normal observation image data G that are respectively an R component and a G component of normal observation image data in an RGB color space obtained by imaging the biological tissue illuminated by the white light, and being color image data Y of an image that has a component in a wavelength region that does not have sensitivity to the first feature amount of the biological tissue but has sensitivity to light scattering by the biological tissue, the first feature amount acquisition unit configured to acquire the first feature amount based on the first parameter.

5. The endoscope system according to claim 1, wherein the imaging unit comprises an R color filter configured to filter light into an R wavelength region in the RGB color space before the light is received by the image sensor, and the first normal observation image data R is data of an image captured via the R color filter of the image sensor.

6. The endoscope system according to claim 1, wherein the light source apparatus comprises:

a white light source that emits white light; and a first optical filter configured to obtain the first special light from the white light, and the light source apparatus switches between emitting the white light and the first special light.

7. The endoscope system according to claim 1, wherein the processor comprises a storage unit that stores data expressing a quantitative relationship between the first parameter and the first feature amount, and the first feature amount acquisition unit is configured to obtain the first feature amount by referencing the data expressing the quantitative relationship.

8. The endoscope system according to claim 1, wherein the first feature amount is a total hemoglobin amount.

9. The endoscope system according to claim 1, wherein the first feature amount is a total hemoglobin amount, and the first special observation image data W is data regarding a wavelength region identical to a G wavelength region in the RGB color space.

10. The endoscope system according to claim 9, wherein the imaging unit comprises a G color filter configured to filter light into a G wavelength region in the RGB color space before the light is received by the image sensor, and the first special observation image data W is data of an image captured by the image sensor via the G color filter.

11. The endoscope system according to claim 1, wherein the processor comprises:

a second parameter generation unit configured to generate a second parameter that has sensitivity to a second feature amount of the biological tissue but does not have sensitivity to the light scattering based on the color image data; and a second feature amount acquisition unit configured to acquire the second feature amount based on the first feature amount and the second parameter.

12. The endoscope system according to claim 1, wherein the feature amount acquisition unit comprises:

a second parameter generation unit configured to generate a second parameter that has sensitivity to a second feature amount of the biological tissue but does not have sensitivity to the light scattering based on the color image data; and a second feature amount acquisition unit configured to acquire the second feature amount based on the first feature amount and the second parameter, the light source apparatus is configured to emit second special light that has a different wavelength region from white light, and is absorbed by the biological tissue differently according to the second feature amount, and the second parameter is a ratio N/W of second special observation image data N obtained by imaging the biological tissue illuminated by the second special light and first special observation image data W obtained by imaging the biological tissue illuminated by the first special light.

13. The endoscope system according to claim 12, wherein a wavelength region of the first special light is set such that absorption of the first special light by the biological tissue is dependent on the first feature amount but not dependent on the second feature amount.

14. The endoscope system according to claim 13, wherein a wavelength region of the second special light is set such that absorption of the second special light by the biological tissue is dependent on both the first feature amount and the second feature amount.

15. The endoscope system according to claim 11, wherein the second feature amount is a degree of oxygen saturation.

16. The endoscope system according to claim 15, wherein the second special observation image data N is image data regarding a wavelength region identical to a G wavelength region in the RGB color space.

17. The endoscope system according to claim 16, wherein the imaging unit comprises a G color filter configured to filter light into a G wavelength region in the RGB color space before the light is received by the image sensor, and the second special observation image data N is data of an image captured via the G color filter.

18. The endoscope system according to claim 1, comprising a feature amount distribution image generation unit configured to generate a feature amount distribution image that expresses a distribution of the first feature amount in the biological tissue based on the first feature amount.

19. The endoscope system according to claim 11, comprising a feature amount distribution image generation unit configured to generate a feature amount distribution image that expresses a distribution of the second feature amount in the biological tissue based on the second feature amount.

* * * * *